US009764309B2

(12) United States Patent
Fonfe et al.

(10) Patent No.: US 9,764,309 B2
(45) Date of Patent: Sep. 19, 2017

(54) CATALYST FOR THE SYNTHESIS OF ALKYL MERCAPTANS AND PROCESS FOR PRODUCING IT

(71) Applicants: Benjamin Fonfe, Frankfurt (DE); Sebastian Fuss, Flieden (DE); Frank Wilz, Alzenau (DE); Harald Jakob, Hasselroth (DE); Christoph Weckbecker, Gruendau (DE)

(72) Inventors: Benjamin Fonfe, Frankfurt (DE); Sebastian Fuss, Flieden (DE); Frank Wilz, Alzenau (DE); Harald Jakob, Hasselroth (DE); Christoph Weckbecker, Gruendau (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/365,801

(22) PCT Filed: Nov. 27, 2012

(86) PCT No.: PCT/EP2012/073724
§ 371 (c)(1),
(2) Date: Jun. 16, 2014

(87) PCT Pub. No.: WO2013/092129
PCT Pub. Date: Jun. 27, 2013

(65) Prior Publication Data
US 2014/0357897 A1  Dec. 4, 2014

(30) Foreign Application Priority Data
Dec. 19, 2011  (EP) .................................. 11194327

(51) Int. Cl.
*B01J 23/30*  (2006.01)
*C07C 319/02*  (2006.01)
(Continued)

(52) U.S. Cl.
CPC .......... *B01J 23/30* (2013.01); *B01J 35/0026* (2013.01); *B01J 35/023* (2013.01);
(Continued)

(58) Field of Classification Search
CPC .......... B01J 23/04; B01J 23/30; C07C 319/02
See application file for complete search history.

(56) References Cited

U.S. PATENT DOCUMENTS 3,312,751 A * 4/1967 Kerr ...................... B01J 29/082
568/73
5,847,223 A  12/1998 Ponceblanc et al.
(Continued)

FOREIGN PATENT DOCUMENTS

CN  1141915 A  2/1997
CN  1780814 A  5/2006
(Continued)

OTHER PUBLICATIONS

Combined Chinese Office Action and Search Report issued Aug. 14, 2015 in Patent Application No. 201280062865.X (with English translation of categories of cited documents).
(Continued)

*Primary Examiner* — Jun Li
(74) *Attorney, Agent, or Firm* — Oblon, McClelland, Maier & Neustadt, L.L.P.

(57) ABSTRACT

The present invention relates to a catalyst which comprises a support material and an oxidic composition containing at least one alkali metal and tungsten, a process for producing such catalysts and also a process for preparing alkyl mercaptans by reaction of alkanols with hydrogen sulphide in the presence of such a catalyst.

18 Claims, 18 Drawing Sheets

(51) Int. Cl.
*B01J 35/00* (2006.01)
*B01J 35/02* (2006.01)
*B01J 35/10* (2006.01)
*B01J 37/00* (2006.01)
*C07C 319/08* (2006.01)
*B01J 37/02* (2006.01)

(52) U.S. Cl.
CPC ....... *B01J 35/1019* (2013.01); *B01J 35/1042* (2013.01); *B01J 37/0036* (2013.01); *C07C 319/02* (2013.01); *C07C 319/08* (2013.01); *B01J 37/0205* (2013.01)

(56) References Cited

U.S. PATENT DOCUMENTS

| | | | |
|---|---|---|---|
| 2004/0132832 A1* | 7/2004 | Espinoza | B01J 21/04 518/716 |
| 2006/0199730 A1* | 9/2006 | Seely | B01J 23/002 502/246 |
| 2007/0015941 A1 | 1/2007 | Brand et al. | |
| 2008/0262270 A1* | 10/2008 | Barth | B01J 23/34 568/70 |
| 2008/0293974 A1* | 11/2008 | Barth | C07C 319/02 568/70 |
| 2009/0118531 A1 | 5/2009 | Hibst et al. | |
| 2010/0248952 A1* | 9/2010 | Redlingshofer | B01J 23/30 502/317 |

FOREIGN PATENT DOCUMENTS

| | | |
|---|---|---|
| CN | 1993177 A | 7/2007 |
| CN | 101432067 A | 5/2009 |
| WO | 99/14172 A2 | 3/1999 |
| WO | 2004/096760 A1 | 11/2004 |
| WO | 2007/125052 A1 | 11/2007 |

OTHER PUBLICATIONS

International Search Report issued Feb. 8, 2013, in PCT/EP2012/073724 filed Nov. 27, 2012.
Written Opinion of the International Searching Authority issued Feb. 8, 2013 in PCT/EP2012/073724 filed Nov. 27, 2012.

* cited by examiner

Fig. 6 a) Material contrast image
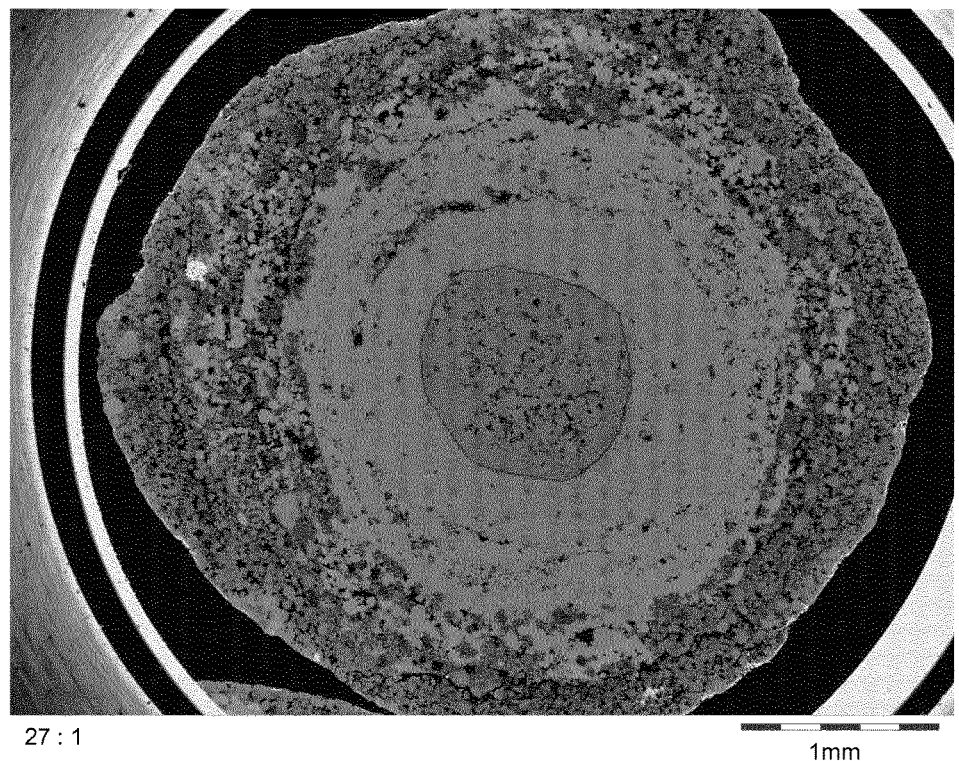
27 : 1
1mm
Fig. 6 b) EDX mapping of Cs
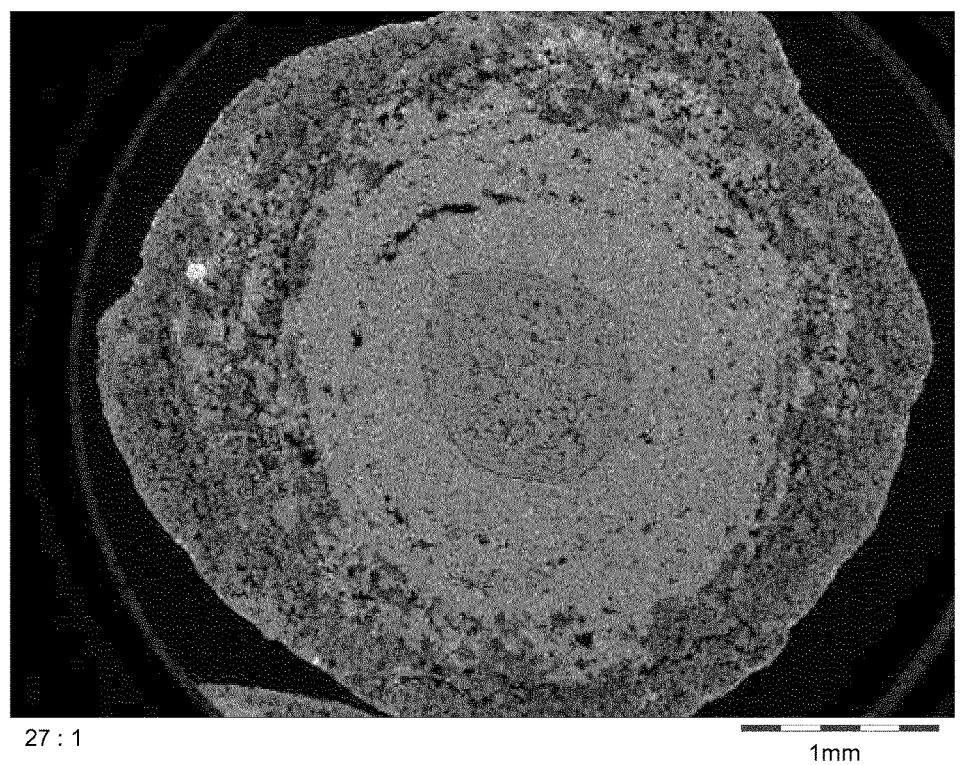
27 : 1
1mm Fig. 6 c) EDX mapping of W
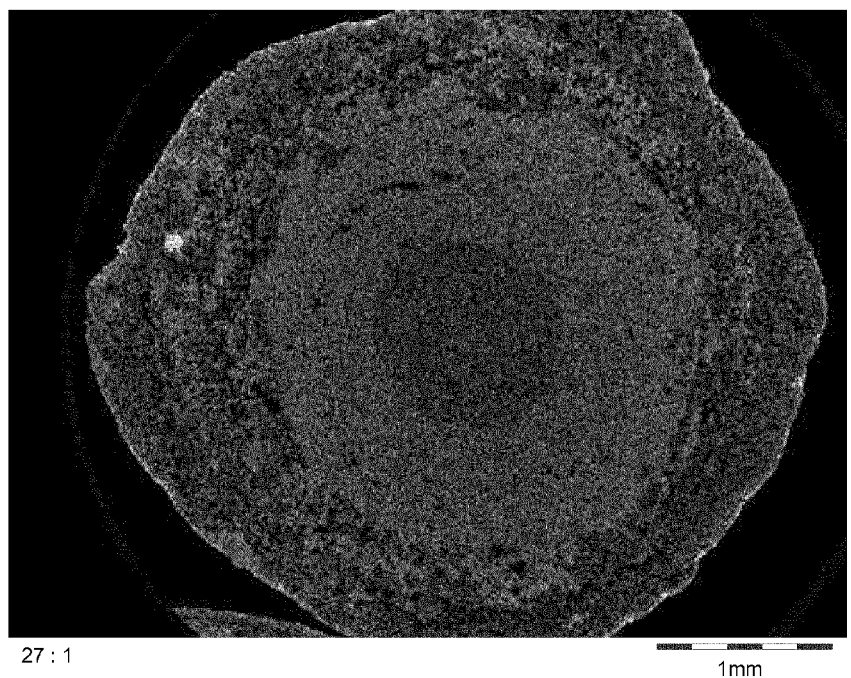

Fig. 6 d) EDX mapping of Al
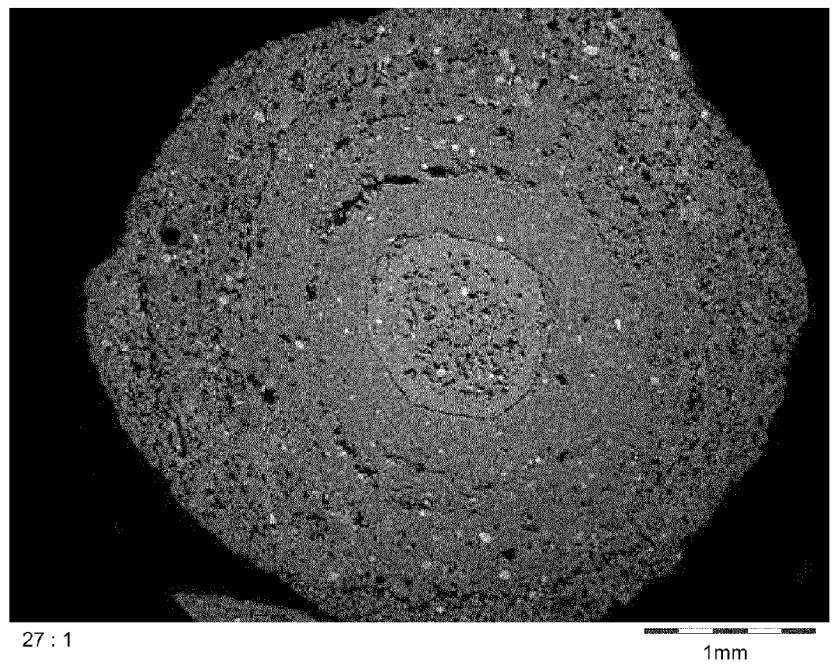
27 : 1  1mm
Fig. 6 e)
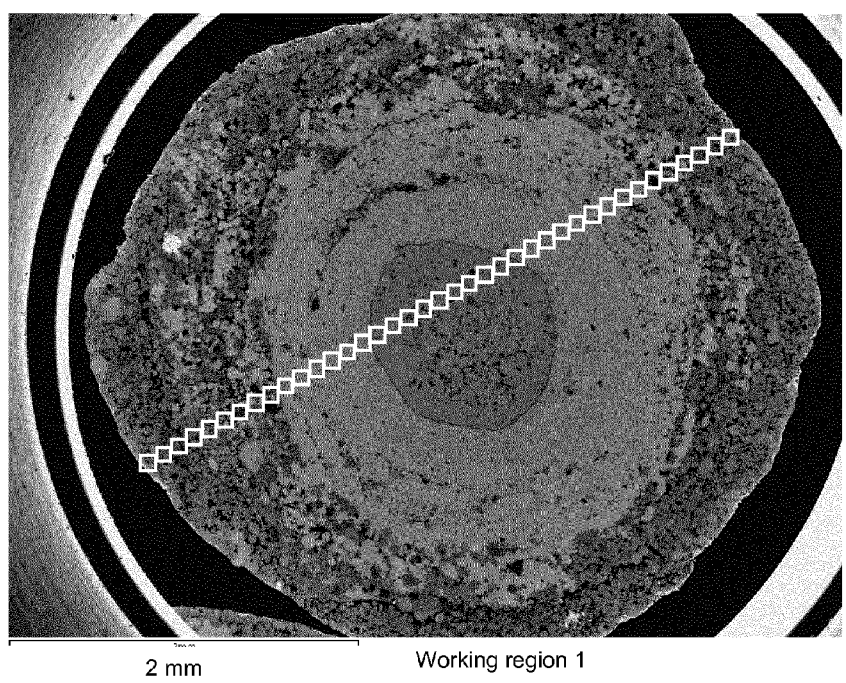
2 mm  Working region 1

MP stands for measurement spots.

Fig. 7 a) Material contrast image
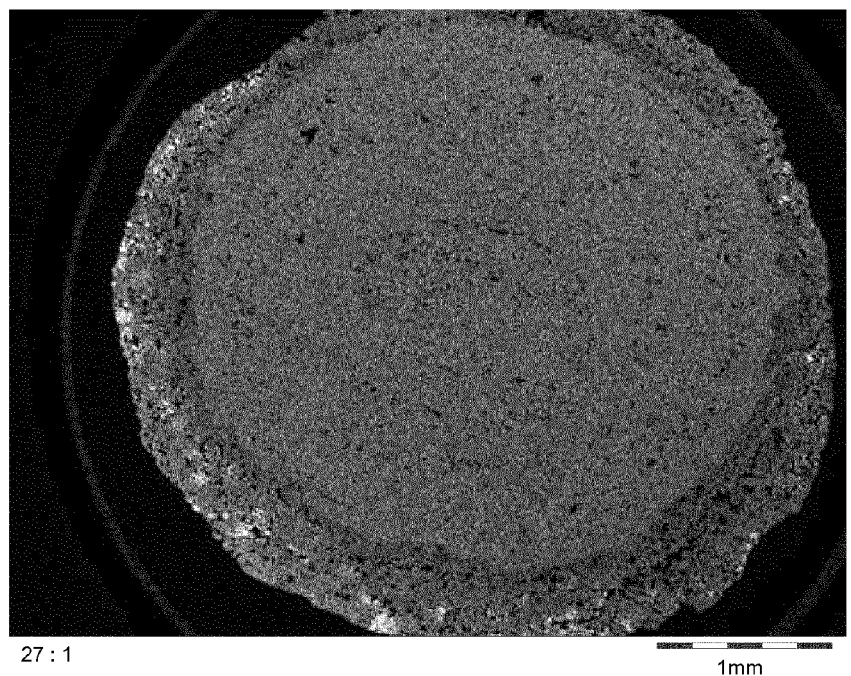
27 : 1
1mm

Fig. 7 b) EDX mapping of Cs
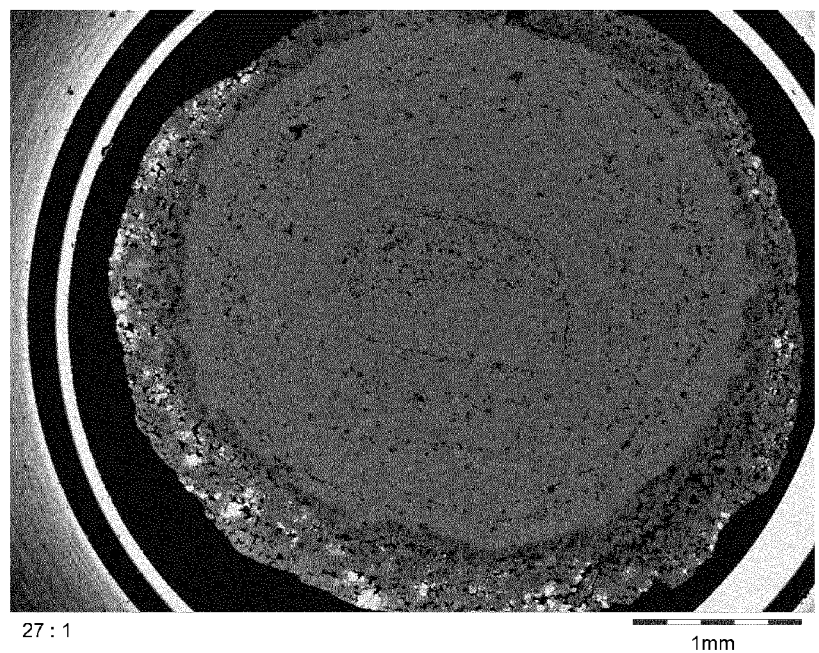

Fig. 7 c) EDX mapping of W
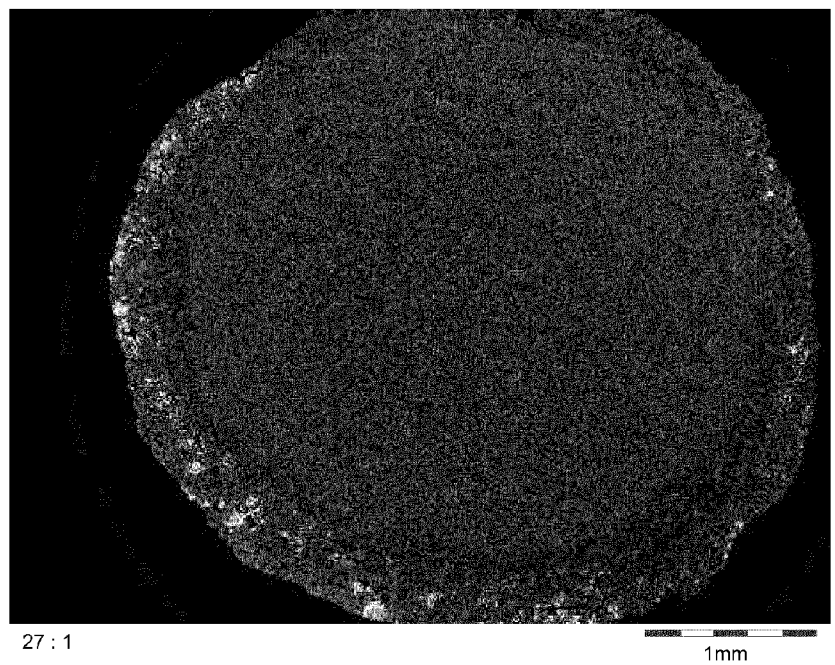
Fig. 7 d) EDX mapping of Al

2 mm    Working region 1

MP stands for measurement spots.

Fig. 8 a) Material contrast image
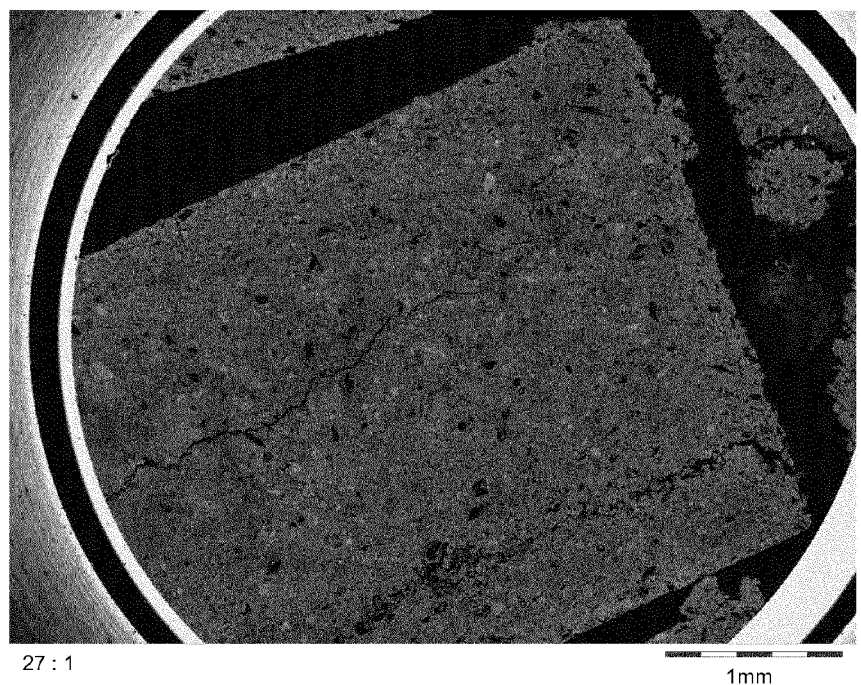

Fig. 8 b) EDX mapping of Cs
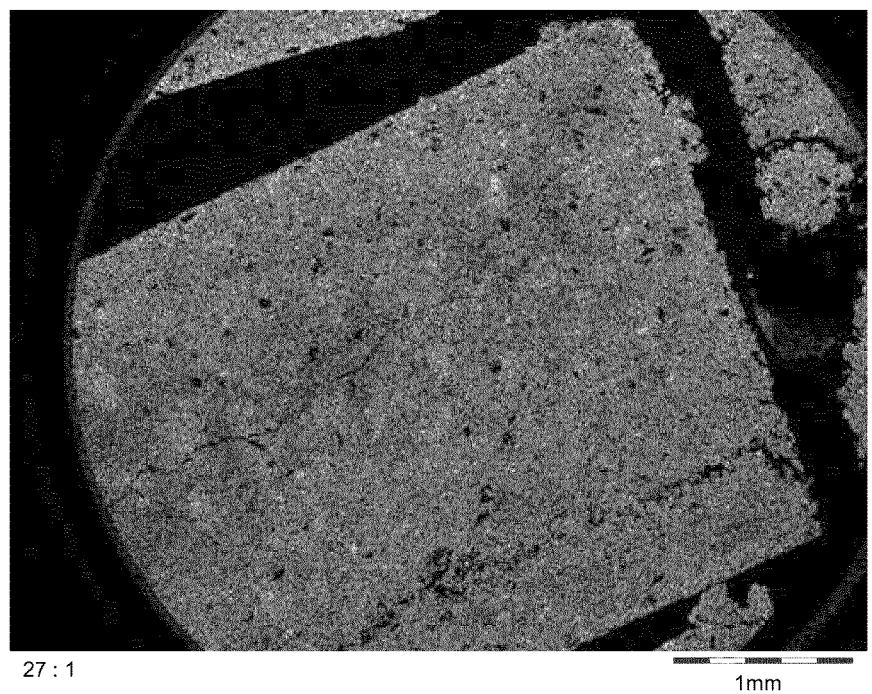
27 : 1
1mm

Fig. 8 c) EDX mapping of W
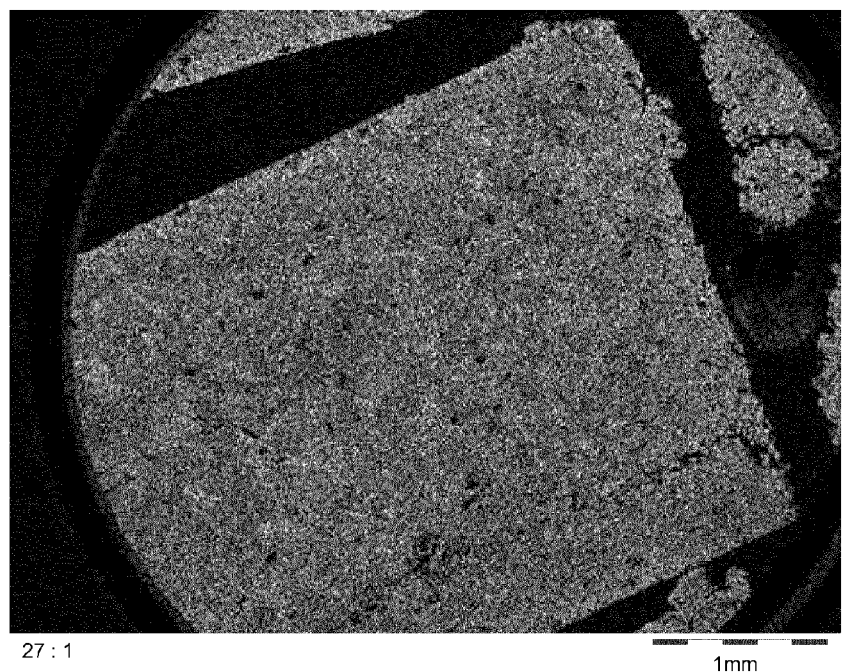

Fig. 8 d) EDX mapping of Al
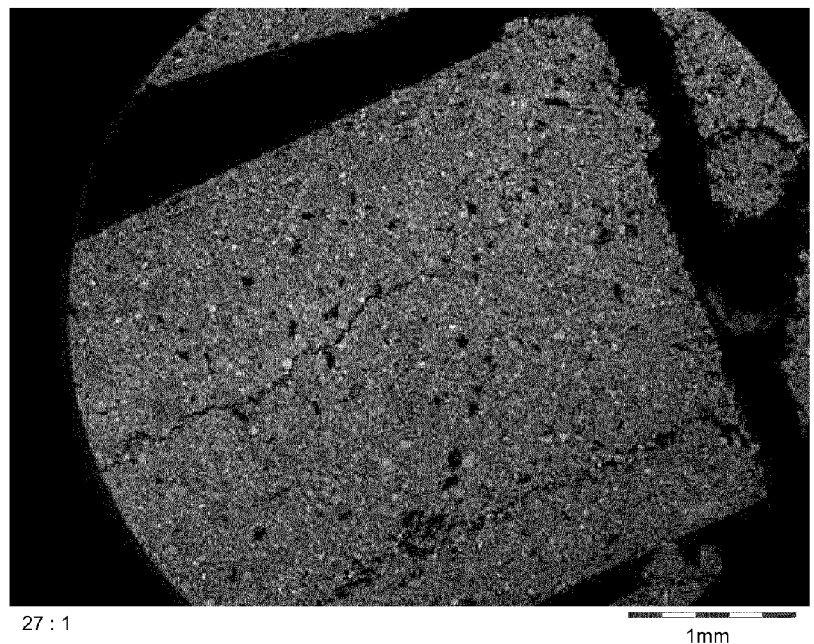
27 : 1
1mm
Fig. 8 e)
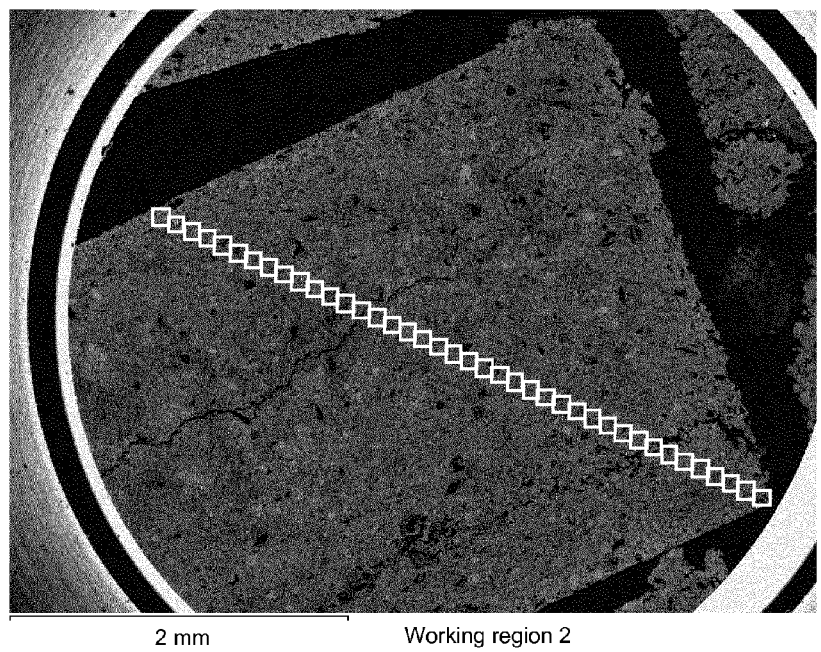
2 mm   Working region 2

MP stands for measurement spots.

CATALYST FOR THE SYNTHESIS OF ALKYL MERCAPTANS AND PROCESS FOR PRODUCING IT

The present invention relates to a catalyst which comprises a support material and an oxidic composition containing at least one alkali metal and tungsten, a process for producing such catalysts and also a process for preparing alkyl mercaptans by reaction of alkanols with hydrogen sulphide in the presence of such a catalyst.

Methyl mercaptan in particular is an industrially important intermediate, for example for the synthesis of methionine, dimethyl sulphoxide or dimethyl sulphone. Methyl mercaptan is nowadays prepared from methanol and hydrogen sulphide by reaction in the presence of a catalyst composed of aluminium oxide. The synthesis of methyl mercaptan is usually carried out in the gas phase at temperatures in the range from 300 to 500° C. and a pressure in the range from 1 to 25 bar.

The reaction mixture obtained here contains the desired product methyl mercaptan together with unreacted starting materials and by-products, for example dimethyl sulphide and dimethyl ether, and also gases which are inert in respect of the reaction, for example methane, carbon monoxide, hydrogen and nitrogen. The methyl mercaptan formed has to be separated off from this reaction mixture.

For the process to have good economics, it is therefore necessary to have both a high conversion and a high selectivity of the catalytic reaction of methanol and hydrogen sulphide to form methyl mercaptan in order to keep the outlay for the separation of the methyl mercaptan formed from the reaction mixture as low as possible. The separation from the reaction gas mixture is usually effected by condensation of the methyl mercaptan, and here the energy consumption for cooling of the reaction mixture, in particular, represents a large cost factor.

To increase the activity and selectivity of the catalyst, aluminium oxide is usually admixed with an alkali metal tungstate (usually also referred to as promoter), for example potassium tungstate or caesium tungstate. The proportion of the tungstate, based on the total weight of the catalyst, is usually up to about 20%, as described, for example, in the U.S. Pat. No. 2,820,062.

The proportion of the alkali metal tungstate in the catalyst can be increased to 25% by weight and more by means of specific processes for producing the catalyst, in which the support material is multiply impregnated with a solution of the alkali metal tungstate in a comparatively complicated process (see, for example, EP 0 832 878 A2 and DE 103 38 887 A1); increasing the concentration of the alkali metal tungstate above a proportion of about 25% by weight brings about an increase in the selectivity only together with an lower activity if the alkali metal and tungsten in the oxidic composition are applied to the catalyst in a stoichiometric ratio of 2:1 (see DE 103 38 887 A1). Although the loading can be increased to more than 35% by weight by use of a nonstoichiometric ratio of caesium and tungsten in the solution used for the impregnation, a significant increase in the conversion or the selectivity can no longer be observed at such high loadings; particularly at loadings above 45% by weight, based on the total weight of the catalyst, conversion and selectivity even decrease.

It was therefore an object of the present invention to provide a catalyst and a process for producing it, which catalyst displays an improved activity and selectivity compared to catalysts known from the prior art for the reaction of hydrogen sulphide with alkanols, in particular with methanol, to form alkyl mercaptans, in particular methyl mercaptan. The improved activity and selectivity should be present at all molar ratios of hydrogen sulphide to methanol customarily used in processes for the synthesis of alkyl mercaptans, for example in the $H_2S$:MeOH range from ≥1:1 to ≤10:1 and in particular also at comparatively low molar ratios of hydrogen sulphide to methanol, i.e. at an $H_2S$:MeOH ratio of ≤3:1, preferably ≤2:1.

It has now surprisingly been found that this object is achieved by a process for producing a catalyst comprising a support material and an oxidic composition containing oxygen together with at least one alkali metal and tungsten, said process comprising the steps:

1) provision of at least one support material, an oxidic tungsten compound and at least one separate alkali metal compound,
2) mixing of the support material with the oxidic tungsten compound and the at least one separate alkali metal compound in order to obtain a catalyst composition and
3) shaping of the catalyst composition obtained, and also the catalysts produced by this process.

In the processes known from the prior art which involve an alkali metal tungstate and a support material such as aluminium oxide, a solution of the alkali metal tungstate is always produced first and is then added to the support material. This solution is then usually applied to particles of the support material having a size of a number of millimeters in an impregnation process, preferably a multistage impregnation process.

It has now surprisingly been found that an increased activity and selectivity of the catalyst can be obtained when the support material is not impregnated with a solution containing both the alkali metal and the tungstate, but instead the support material is mixed with an oxidic tungsten compound which preferably does not contain any alkali metal and with a separate alkali metal compound.

The catalysts produced by the process of the invention make it possible to achieve a higher conversion and a greater selectivity under identical reaction conditions and the same loading compared to catalysts known from the prior art which have been produced by the impregnation process.

Furthermore, the process of the invention allows simple variation of the ratio of the content of alkali metal to the content of tungsten in the oxidic composition, expressed as ratio of alkali metal oxide $A_2O$ in % by weight, based on the total mass of the catalyst, to tungsten(VI) oxide $WO_3$ in % by weight, based on the total mass of the catalyst. The total loading of the catalyst with the oxidic composition containing the alkali metal and tungsten is the sum of the above-mentioned proportions of $A_2O$ and $WO_3$ in the catalyst. The advantages of a nonstoichiometric ratio have been described in the patent application DE 103 38 887 A1.

The process of the invention also makes it possible to obtain high loadings of the support material with the oxidic composition containing the alkali metal and tungsten without a multistage, very time-consuming impregnation process having to be carried out.

Furthermore, the present process even makes it possible to obtain catalysts which have a loading of over 45% by weight of the oxidic composition and display both a good activity and a good selectivity.

A further advantage of the catalysts of the present invention is the fact that they provide catalysts which enable selectivities of above 95% at a conversion of likewise above 95% to be achieved in the reaction of alkanols and hydrogen sulphide to form alkyl mercaptans under typical reaction conditions. The catalysts of the invention allow, for example, the reaction of hydrogen sulphide and methanol to form methyl mercaptan to be carried out at a selectivity of significantly above 95% at a conversion of likewise above 95% under typical reaction conditions (temperature from about 300 to 370° C., pressure about 9 bar, mass ratio of $H_2S$/MeOH about 1.9), as the examples according to the invention demonstrate. The catalysts of the invention sometimes allow a selectivity of above 96% to be achieved at a conversion of above 99% even at a ratio of $H_2S$:MeOH of <2:1. At higher ratios of $H_2S$:MeOH, i.e. $H_2S$:MeOH>2:1, the results are even better.

The high selectivity at a high conversion and comparatively low ratios of $H_2S$:MeOH (for example ≤3:1) allows, inter alia, an efficient synthesis of alkyl mercaptans at a conversion of ≥98%, as a result of which the separation of the alkyl mercaptan from the reaction mixture is considerably simplified.

For the purposes of the present invention, the term conversion refers to the ratio of the amount of methanol reacted during the course of the catalysed reaction, i.e. amount of methanol which has actually reacted, to the amount of methanol used. This can be determined, for example, by gas chromatography.

For the purposes of the present invention, the term selectivity refers to the ratio of the amount of methyl mercaptan formed to the amount of methanol reacted.

The oxidic composition containing oxygen together with at least one alkali metal and tungsten encompasses, for the purposes of the present invention, both alkali metal tungstates having stoichiometric ratios of alkali metal and tungsten, for example $A_2WO_4$ (or $A_2O+WO_3$), where A is an alkali metal, and also mixed oxides containing tungsten and at least one alkali metal and having the general formula $A_xWO_y$, where the symbols have the following meanings
A: at least one alkali metal, preferably selected from the group consisting of sodium, potassium, rubidium and caesium,
x: mole fraction of the at least one alkali metal relative to tungsten in the composition, which is preferably in the range from 2:1 to 0.8:1, particularly preferably in the range from 1.9:1 to 1.1:1, and
y: mole fraction of oxygen in the composition, which is preferably in the range from 3.4 to 4,
and also intimate mixtures of alkali metal oxides and oxidic tungsten compounds. For the purposes of the present invention, mixed oxides are substances which contain oxides of a plurality of different chemical elements which are intimately mixed at a moleclular level.

For the purposes of present invention, a separate alkali metal compound is a chemical compound which contains at least one alkali metal and is physically separate from the oxidic tungsten compound, i.e. in particular not in the form of a solution containing alkali metal ions together with a tungsten compound or tungsten ions.

The oxidic tungsten compound used in the process of the invention is preferably a compound containing tungsten in the oxidation state VI. The oxidic tungsten compound is preferably selected from the group consisting of tungsten trioxide ($WO_3$), tungstic acid ($WO_3.H_2O$), metatungstic acid, paratungstic acid, isopolytungstic acids, heteropolytungstic acids, ammonium salts of these tungstic acids, i.e. ammonium tungstates (orthotungstates, metatungstates and paratungstates), and ammonium isopolytungstates, heteropolytungstates, hydrates of these and mixtures of these and is preferably tungstic acid or ammonium orthotungstate, metatungstate or paratungstate.

The at least one alkali metal compound used in the process of the invention is preferably a water-soluble alkali metal compound. Furthermore, the alkali metal compound is preferably a basic alkali metal compound.

For the purposes of the present invention, basic alkali metal compounds are water-soluble compounds which contain an alkali metal and on dissolution in water give a solution having a pH of >7 at room temperature (23° C.). The alkali metal compound is preferably selected from the group consisting of hydroxides and carbonates of alkali metals. The alkali metal is preferably at least one alkali metal selected from the group consisting of sodium, potassium, caesium and rubidium or a mixture of at least two of these alkali metals. The basic alkali metal compound is particularly preferably a hydroxide or carbonate of an alkali metal selected from the group consisting of sodium, potassium, caesium and rubidium. For the purposes of the present invention, the use of potassium hydroxide, caesium hydroxide or a mixture of potassium hydroxide and caesium hydroxide is very particularly preferred.

The support material in the catalyst of the invention is preferably an oxidic inorganic support material. This is preferably selected from the group consisting of aluminium oxide, silicon dioxide, titanium dioxide, zirconium oxide, amorphous aluminosilicates and mixtures thereof. This support material is preferably used in the form of particles having a size of less than 1000 μm. The support material is particularly preferably aluminium oxide.

The geometric shape of the support material particles is in principle not subject to any restrictions. The particles can, for example, be in the form of spheres, cylinders, cuboids, cubes, prisms, ellipsoids, rings or irregularly shaped particles, without being restricted to these shapes. For the purposes of the present invention, the size of these particles is in each case the largest linear dimension of a particle, i.e., for example, in the case of cuboidal particles the length and in the case of spherical particles the diameter. The size of the particles used in the process of the invention is also preferably less than 500 μm, particularly preferably less than 250 μm, particularly preferably less than 100 μm and in particular less than 50 μm. The size of the particles of support material used is very particularly preferably in the range from 1 to 25 μm.

Active aluminium oxide, which has a high specific surface area in the range from about 10 to about 400 $m^2$/g and consists mainly of oxides of the transition series of the crystallographic phases of aluminium oxide (see Ullmann's Encyclopaedia of Industrial Chemistry, 1985, Vol. A1, 561-562), is particularly preferred as support material. Such transition oxides include γ-, δ-, ε-, κ-, χ- and θ-aluminium oxide. Active aluminium oxide is marketed, in various grades and supplies for catalytic applications. Powders of the corresponding aluminium oxide consisting of particles having a particle size of from about 1 to 25 μm and having a specific surface area in the range from 180 to 400 $m^2$/g, determined in accordance with ISO 9277, a mesopore volume (d=2-50 nm) in the range from 5 to 50 ml/100 g, determined in accordance with DIN 66134, a macropore volume (d>50 nm) in the range from 20 to 100 ml/100 g, determined in accordance with DIN 66133, and a bulk density in the range from 300 to 1000 g/l, determined in accordance with DIN ISO 697, are particularly suitable for producing the catalysts of the invention.

In the process of the invention, the oxidic tungsten compound and the separate alkali metal compound are preferably added in succession to the support material. Here the support material can either firstly be mixed with the oxidic tungsten compound and the resulting mixture can then be mixed with the at least one alkali metal compound. As an alternative, the support material can firstly be mixed with the at least one alkali metal compound and the resulting mixture can subsequently be mixed with the oxidic tungsten compound to form a catalyst composition.

The oxidic tungsten compound is preferably added as a solid to the support material or to the mixture of support material and the at least one alkali metal compound. Particular preference is given to addition of solid tungstic acid before or after addition of an aqueous solution of an alkali metal hydroxide having a concentration of alkali metal hydroxide, based on the total weight of the solution, of ≥50% by weight. Particular preference is given to adding solid tungstic acid before or after a 70% strength aqueous alkali metal hydroxide solution to the support material.

Shaping of the catalyst is preferably carried out by extrusion of the catalyst composition obtained or pressing of this, for example in a tabletting press. The temperature should preferably not exceed 40° C. during extrusion. The pressure here is preferably at least 5 bar.

The catalyst produced by the process of the invention is preferably an all-active catalyst, i.e. a catalyst in which the catalyst composition is homogeneously distributed throughout the entire shaped catalyst body, which is preferably in the form of extrudates or pressed bodies, in contrast to a coated catalyst in which a mixture containing the oxidic composition is applied in the form of a shell to a support.

The process of the invention is preferably employed for producing catalysts for use in a fixed-bed reactor, which are preferably in the form of discrete catalyst particles. These catalyst particles preferably have a size in the range from 1 to 9 mm, particularly preferably from 1.5 to 5 mm.

The geometric shape of these catalyst particles is in principle not subject to any restriction. The catalyst particles can, for example, be in the form of spheres, cylinders, cuboids, cubes, prisms, ellipsoids, rings or irregularly shaped particles, without being restricted to these shapes.

The bulk density of the catalyst material obtained in this way is preferably greater than 0.70 g/cm$^3$, more preferably greater than 0.80 g/cm$^3$, particularly preferably greater than 0.9 g/cm$^3$ and in particular from 1.0 to 1.7 g/cm$^3$ (determined in accordance with DIN ISO 697).

The specific BET surface area of the catalyst can be less than 180 m$^2$/g, determined in accordance with ISO 9277, and even less than 90 m$^2$/g, but is in any case greater than 10 m$^2$/g. It is preferably 30-80 m$^2$/g, particularly preferably 40-60 m$^2$/g.

This is all the more surprising since very good results are also achieved at these comparatively low values for the BET surface area, while the BET surface area of the catalysts known from the prior art is generally 140 and more g/m$^2$ and in the case of these, better results are obtained, the higher the BET surface area.

The specific pore volume of the mesopores of the catalyst, i.e. the pores having a diameter in the range from 2 to 50 nm, is preferably less than 0.20 ml/g, particularly preferably less than 0.15 ml/g, determined by the method of Barrett, Joyner and Halenda (BJH) in accordance with DIN 66134.

The specific pore volume of the macropores of the catalyst, i.e. the pores having a diameter above 50 nm, is preferably less than 0.40 ml/g, particularly preferably less than 0.25 ml/g, determined by mercury intrusion in accordance with DIN 66133.

The process of the invention for producing the catalyst preferably also comprises at least one, preferably both, of the following additional steps: (i) drying of the catalyst composition and/or of the shaped catalyst and (ii) calcination of the catalyst composition and/or of the shaped catalyst.

Drying and calcination can, as one alternative, be carried out on the catalyst composition which has not yet been shaped to form catalyst particles, i.e. after Step 2 and before Step 3 of the process of the invention. This is preferably the case when the catalyst composition is to be shaped by pressing. Drying and calcination can also be carried out on the previously shaped catalyst particles, i.e. after Step 3 of the process of the invention. The latter is preferably the case when shaping of the catalyst composition is carried out by means of extrusion.

The process of the invention for producing the catalyst preferably also comprises that the shaping of the catalyst is carried out by extrusion or pressing and the process preferably comprises the following additional steps:
(i) drying of the catalyst composition and/or of the shaped catalyst, and
(ii) calcination of the catalyst composition and/or of the shaped catalyst.

Furthermore, the catalyst composition or the shaped catalyst can also be predried at room temperature for a time of from about 1 to 10 hours.

Actual drying is preferably carried out for a time of from 1 to 10 hours at a temperature of from 100 to 200° C., particularly preferably at a temperature of from 100 to 140° C. Calcination is preferably carried out for a time of from 1 to 20 hours, preferably from 1 to 10 hours and particularly preferably from 1 to 5 hours, at a temperature of from 300 to 600° C., particularly preferably at a temperature of from 420 to 480° C. Both drying and calcination can, for example, be carried out in a muffle furnace, with calcination also being able to follow directly after drying without the catalyst being cooled in between. A gas stream can optionally be passed through the bed of the catalyst during predrying, drying and/or calcination so as to aid removal of the residual moisture. Suitable gases are, for example, air, carbon dioxide, nitrogen, noble gases, etc., without being restricted thereto.

In the process of the invention, further materials such as solvents, binders, pressing aids, pore formers, mineral fibres or lubricants can also be added to the catalyst composition in one of the above-described steps of mixing of individual constituents of the catalyst composition (Step 2) or of shaping of the catalyst (Step 3). Preference is given to at least one organic and/or inorganic binder and/or mineral fibres being added to the mixture of support material with tungstic acid and/or alkali metal compound in one or both of the abovementioned Steps 2 and 3. Suitable binders encompass, for example, colloidal silica dispersions, high-polymer polysaccharides such as hydroxyethylcellulose or methylhydroxyethylcellulose and wax dispersions, without being restricted to these.

As binder, preference is given to using at least one colloidal silica dispersion, particularly preferably in combination with organic binders. The proportion of binder or binders, if a plurality are used, in the composition of the invention is preferably from 0.1 to 20% by weight, based on the total composition, particularly preferably from 1 to 10% by weight. If a colloidal silica dispersion is used as binder, the proportion of this binder in the dried, calcined and shaped catalyst is preferably from 3 to 7% and in particular from 4 to 6%, based on the SiO$_2$ content of the total support composition.

The proportion of support material in the catalyst particles according to the invention is preferably from 20 to 85% by weight, particularly preferably from 25 to 50% by weight, based on the total composition.

The present invention further provides a catalyst for preparing alkyl mercaptans by reaction of alkanols with hydrogen sulphide, which catalyst comprises a support material and an oxidic composition containing oxygen together with at least one alkali metal and tungsten and has been produced from particles of the support material having a particle size of less than 1000 µm, preferably less than 500 µm, more preferably less than 250 µm, particularly preferably less than 100 µm, and in particular is composed of particles having a particle size in the range from 1 to 25 µm.

The catalyst is preferably a catalyst in which the standard deviation stadev of the normalized tungsten concentration ($c_{norm}$ (W)) over the cross section of the catalyst is less than 20.0, determined by quantitative EDX analysis in accordance with ISO 22309 (2006) in square measurement spots, preferably at least 10 square measurement spots, which have a side length of 100 µm in each case and whose midpoints lie on a straight line and are in each case 100 µm from the midpoint of the adjoining square, with the first and last midpoint of a square being in each case about 100 µm from the edge of the measured catalyst cross section. For the purposes of the invention, the normalized concentration $c_{norm}$ is the ratio of the experimentally determined concentration of the element concerned in the respective square and the average of the concentration of this element over the cross section of the specimen, i.e. the sum of all measured square spots, multiplied by the factor 100.

The number and position of the square measurement spots is determined to a certain extent by the size and shape of the catalyst particle, but the number is preferably at least 15, more preferably at least 20, particularly preferably at least 25 and in particular at least 30, and preferably not more than 200, more preferably not more than 150, particularly preferably not more than 100 and in particular not more than 50. Very particular preference can be given, for example, to a value of 40+/−2 measurement spots. In the case of a spherical catalyst particle, the straight line defined by the midpoints of the measured squares preferably runs through the centre of the sphere, and its length corresponds to the sphere diameter. In the case of a catalyst particle having a shape deviating from a spherical shape, for example an extrudate, the straight line defined by the midpoints of the measured squares preferably intersects at least the longitudinal axis of the particle, particularly preferably at the geometric centre of gravity of the particle, with the length of this straight line being at least the length of the diameter of the cross section. The straight line defined by the midpoints of the measured squares can, however, also be identical to the longitudinal axis.

The average deviation, i.e. the average absolute deviation from the average, of the tungsten concentration determined in this way is preferably less than 15.0 and/or the difference between the maximum value of the normalized tungsten concentration determined and the minimum value Δ (max-min) is preferably less than 90.0.

The standard deviation of the caesium concentration determined in this way is preferably less than 15.5 and the difference between the maximum and the minimum of the normalized caesium concentration is less than 64.0.

The determination of the abovementioned parameters is illustrated in the following examples.

The oxidic composition is preferably a composition of the general formula $A_xWO_y$, where the symbols have the following meanings A: at least one alkali metal, preferably selected from the group consisting of sodium, potassium, rubidium and caesium, x: mole fraction of the at least one alkali metal relative to tungsten in the composition, which is preferably in the range from 2:1 to 0.8:1, particularly preferably in the range from 1.9:1 to 1.1:1, and y: mole fraction of oxygen in the composition, which is preferably in the range from 3.4 to 4.

The oxidic composition in the catalyst corresponds to that defined above for the process of the invention.

The catalyst of the invention is preferably produced by a process which comprises a step of mixing a solid tungsten compound, preferably a solid oxidic tungsten compound, with the support material, as has been described above. The oxidic tungsten compound is preferably one of the above-described tungsten compounds.

The proportion of the oxidic composition composed of alkali metal and tungsten in the catalyst is preferably greater than 15% by weight, more preferably greater than 25% by weight, more preferably greater than 36% by weight, particularly preferably greater than 40% by weight and in particular greater than 45% by weight, based on the total weight of the catalyst. The proportion of the oxidic composition in the catalyst is preferably up to 60% by weight.

The support material comprises at least one oxidic inorganic compound which is particularly preferably selected from the group consisting of aluminium oxide, silicon oxide, titanium dioxide, zirconium oxide, amorphous aluminium silicates and mixtures thereof. Preferred embodiments of this support material have been described above for the process of the invention.

The catalyst of the invention preferably further comprises at least one organic and/or inorganic binder, where these binders are preferably one of the abovementioned binders and are preferably present in the catalyst composition in the abovementioned proportions by weight.

The catalyst of the invention is preferably produced by the above-described process of the invention for producing a catalyst.

The invention further provides a process for preparing alkyl mercaptans by reaction of alkanols with hydrogen sulphide, preferably for preparing methyl mercaptan by reaction of methanol with hydrogen sulphide, in the presence of the catalyst of the invention or a catalyst which has been produced by the process of the invention for producing a catalyst.

This process is preferably carried out at a temperature of from 250 to 500° C., particularly preferably from 300 to 400° C. The mass ratio of hydrogen sulphide to methanol is preferably in the range from 1:1 to 10:1, more preferably in the range from 1:1 to 5:1, particularly preferably in the range from 1:1 to ≤3:1 and in particular in the range from 1:1 to ≤2:1. The reaction is preferably carried out at a pressure in the range from 1 to 20 bar, particularly preferably in the range from 3 to 10 bar. The reaction is preferably carried out at an alkanol conversion of ≥90%, more preferably ≥92.5%, particularly preferably ≥95% and in particular ≥98% or even ≥99%.

DESCRIPTION OF THE FIGURES

FIG. 7: Example 2) compared to a catalyst according to the invention (FIG. 8: Example 6), determined by EDX mapping. As respective FIG. 6a, FIG. 7a, and FIG. 8a, a material contrast image of a catalyst particle in which the substantial homogeneity (FIG. 8a: Example 6) or inhomogeneity (FIG. 6a: Example 1) of the catalyst structure or the distribution of the elements therein can be seen is shown. The respective FIGS. 6 b, 6c, and 6d, FIGS. 7b, 7c, and 7d, and FIGS. 8b, 8c, and 8d show the concentration of the elements caesium (FIGS. 6 b, 7b, and 8b), tungsten (FIGS. 6c, 7 c, and 8c) and aluminium (FIGS. 6 d, 7 d, and 8d) in the catalyst particle. A scale which shows, to scale, the length of one millimeter of the original structure is also shown under the respective figure. The respective FIGS. 6e, 7e, and 8e show the distribution of the measurement squares for quantifying the homogeneity of the distribution of the elements caesium and tungsten over the catalyst cross section, as is described in detail in Example 18; the respective FIGS. 6 f, 7f, 8f show the graphical evaluation of these measurements.

EXAMPLES

Example 1 (Comparative Example)

Figure 1:
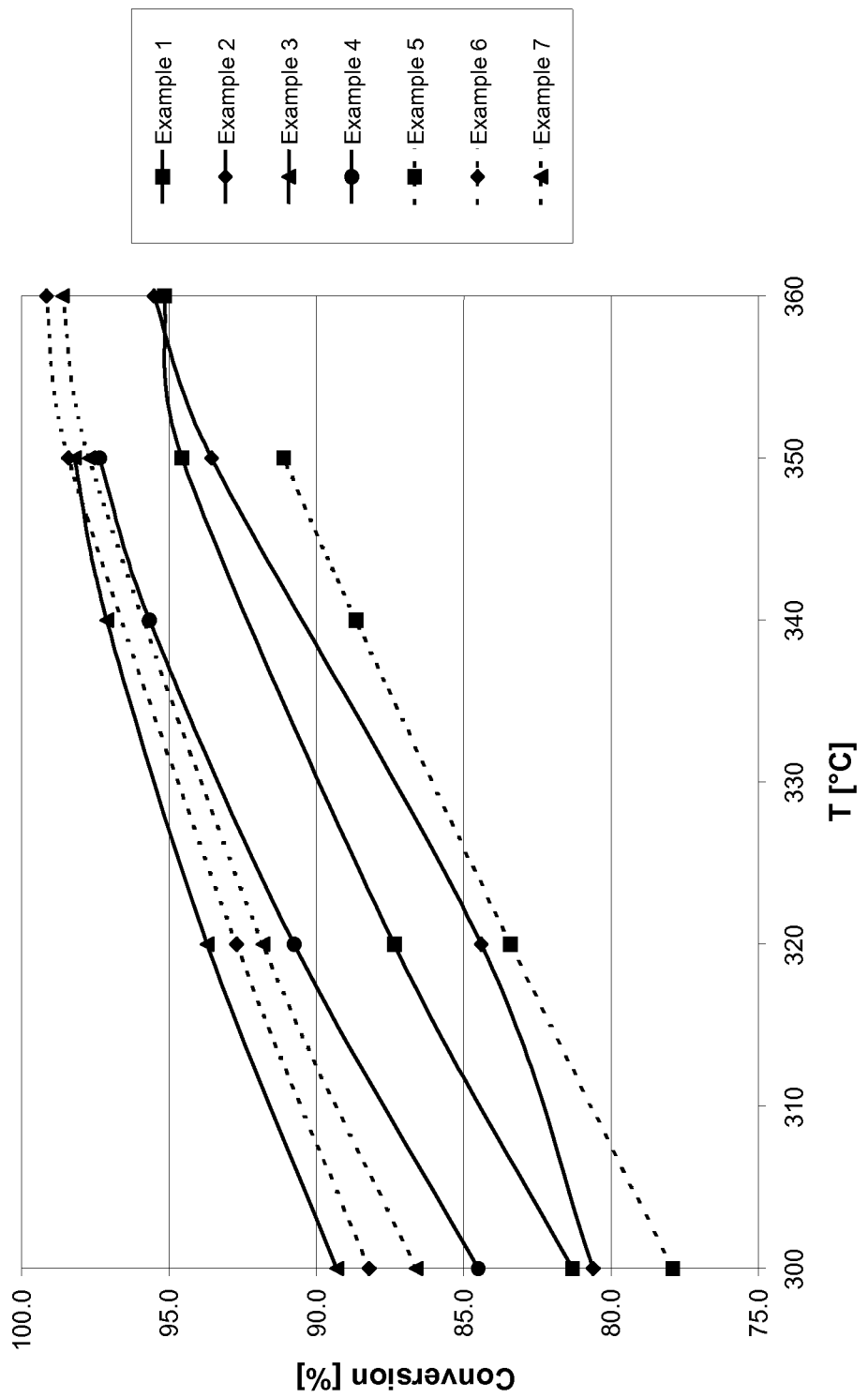
FIG. 1 shows the conversion in the reaction of hydrogen sulphide and methanol to form methyl mercaptan achieved when using the catalysts according to the invention (Examples 3 to 7) at various temperatures under the conditions described in Example 8 compared to that achieved when using catalysts which have been produced by processes known from the prior art (Comparative Examples 1 and 2).

200 g of spherical aluminium oxide having a particle diameter of from 2 to 5 mm (Spheralite 501 A from Axens having a specific surface area of 303 m$^2$/g, a pore volume of 45 ml/100 g and a bulk density of 815 kg/m$^3$) were impregnated in a three-stage impregnation with a total of 52.8% by weight of oxidic composition of the formula $Cs_{1.44}WO_{3.72}$ by means of vacuum impregnation. The following procedure was employed for this purpose: 103.3 g of tungstic acid were suspended in 206.5 g of 32% strength ammonia solution and dissolved by stirring for about 30 minutes. 126.9 g of a 70% strength solution of caesium hydroxide in water were added to the ammonia solution and the resultant solution was stirred for about 23-24 hours. The aluminium oxide was placed in a glass vessel which had been evacuated to 150 mbar. The impregnation solution was drawn in by opening a stopcock until there were about 4.5 cm of impregnation solution over the total aluminium oxide. After admission of air into the glass vessel, the support was incubated in the solution for about 15 minutes. The solution was subsequently drained off and the catalyst was predried for about one hour by passing through a stream of 200 standard l/h (volume flow in the standard state at 0° C. and 1.013 bar absolute in accordance with DIN 1343) of air, with adhering impregnation solution being flushed into the receiver.

The catalyst was subsequently heated at a heating rate of 1° C./min to 120° C. under a stream of 60 m$^3$/h of air and maintained at this temperature for three hours. The temperature was then increased at a heating rate of 5° C./min to 455° C. and the catalyst was calcined at this temperature for 3 hours.

To carry out the second impregnation, an impregnation solution as described above for the first step was made up and applied in the same way by vacuum impregnation to the previously loaded catalyst obtained from the first impregnation. Predrying at room temperature followed by three-stage drying at 120° C. and subsequent calcination at 455° C. for 3 hours were carried out as described above.

The third impregnation was carried out in the same way.

Example 2 (Comparative Example)

Comparative Example 1 was repeated with a loading of 17.8% by weight of $WO_3$ and 17.3% by weight of $Cs_2O$ on the aluminium oxide.

Example 3

In this example according to the invention, 80 g of a pulverulent aluminium oxide having a particle diameter of from 7 to 15 μm (Spheralite 509A from Axens having a specific surface area of 335 m$^2$/g, a pore volume of 56 ml/100 g and a bulk density of 840 kg/m$^3$) were mixed in succession with solid tungstic acid and a calcium hydroxide solution.

For this purpose, the procedure was as follows:

In a glass beaker, 80 g of the aluminium oxide were mixed with 40.98 g of solid tungstic acid. 69.85 g of a 50% strength solution of caesium hydroxide in water and 5.33 g of a 6% strength aqueous methylhydroxyethylcellulose solution (Tylose MH 1000, ShinEtsu, Tokyo, Japan) were added to the pulverulent mixture and the mixture was kneaded with the aid of a spatula for 10 minutes until an extrudable composition was formed, i.e. the liquid had been taken up completely and a dough-like composition which was not sticky had been obtained (about 10 minutes). 5.33 g of petroleum (Merck, Darmstadt, Germany) were added and kneaded into the mixture. The mixture was dried and subsequently calcined in a muffle furnace by firstly heating it at a heating rate of 2° C./min to 120° C., maintaining it at this temperature for 3 hours, then heating it at a heating rate of 5° C./min to 455° C. and maintaining it at this temperature for 3 hours. The mixture was subsequently cooled to 20° C.

After cooling, the granular material obtained was milled in a mortar. From 1 to 2 g of the catalyst powder obtained were subsequently pressed in a tabletting press at a pressure of 4 t for about 1 minute to give a pellet having a diameter of 20 mm.

For subsequent use in a test reactor for preparing methyl mercaptan, the pellet was broken up into pieces having a maximum edge length of 5 mm.

Example 4

Example 3 was repeated with a loading of 17.8% of $WO_3$ and 17.3% by weight of $Cs_2O$ on the aluminium oxide.

Example 5

Example 4 was repeated using aluminium oxide having a particle diameter of less than 250 μm obtained by milling of spherical aluminium oxide having a particle diameter of from 2 to 5 mm (Spheralite 501 A) instead of the pulverulent aluminium oxide having a particle diameter of from 7 to 15 μm (Spheralite 509 A).

Example 6: Production of the Catalyst Particles According to the Invention with Addition of Binders and Shaping by Extrusion 1.05 kg of Spheralite 509 A and 537.9 g tungstic acid were mixed in a laboratory batch kneader (Coperion LUK 2.5, Weinheim, Stuttgart, Germany) at 40 revolutions per minute of the kneading hook and 11 revolutions per minute of the discharge screw (backward-directed), with the barrel of the kneader being cooled to 10° C. by means of a cryostat. 740.5 g of a 70% strength by weight aqueous caesium hydroxide solution were subsequently added over a period of 1 minute with continual mixing, resulting in the temperature rising briefly from 30 to 40° C. 127.5 g of deionized water and then 175 g of a colloidal silica dispersion (Lithosol 1530, Zschimmer & Schwarz GmbH & Co. KG, Lahnstein, Germany) were added 10 minutes after addition was completed. The mixture obtained was mixed for a further 10 minutes before a mixture of 30 g of a high-polymer polysaccharide (Zusoplast PS 1, Zschimmer & Schwarz GmbH & Co. KG, Lahnstein, Germany) and 30 g of hydroxyethylcellulose (Tylose H 10000 P2 ShinEtsu, Tokyo, Japan) were added. The binders were allowed to swell for 120 minutes while kneading the composition continually. 15 g of a nonionic wax dispersion (Zusoplast WEB, Zschimmer & Schwarz GmbH & Co. KG, Lahnstein, Germany) were subsequently added. After a total kneading time of 190 minutes, extrusion was commenced, for which purpose the direction of rotation of the screw was changed over to transport at a constant speed of rotation of the kneader and the speed of rotation of the screw was increased to 13 revolutions per minute. An attachment having four horizontal holes each having a diameter of 3.2 mm was used as pressing tool. Two cutting wires which were cut horizontally were operated at 400 revolutions per minute in order to obtain extrudates having a length of about 3.2 mm. The die pressure was 12.7 bar. The cut extrudates were allowed to fall onto a drying belt and predried at 60° C. before being heated at a heating rate of 1° C./min to 120° C. in a muffle furnace and maintained at this temperature for 3 hours. To carry out calcination, the extrudates were directly afterwards heated at a heating rate of 5° C./min to 455° C. and maintained at this temperature for 3 hours.

Example 7

Example 6 was repeated, this time with the addition of the caesium hydroxide solution being carried out before the addition of the solid tungstic acid.

1.1. Example 8: Use Example

The catalysts produced in Examples 1 to 7 were examined in respect of their performance characteristics in the synthesis of methyl mercaptan from hydrogen sulphide and methanol.

The reaction of hydrogen sulphide and methanol to form methyl mercaptan in the presence of the respective catalyst was carried out in a stainless steel tube having a diameter of 18 mm and a length of 500 mm. A catalyst bed which had a volume of 76 ml and was in each case fixed in the reaction tube by means of inert beds of glass spheres on both sides was used in each case. The reaction tube was heated via a double wall by means of a heat transfer fluid to the various reaction temperatures in the range from 300 to 360° C. indicated in Table 1 below.

TABLE 1

| Catalyst | T [° C.] | Conversion [%] | Selectivity [%] | Support* | WO$_3$ Loading [% by wt.] | Cs$_2$O Loading [% by wt.] |
|---|---|---|---|---|---|---|
| Example 1 (comparative example) | 300 | 81.3 | 95.9 | I (imp) | 28.20 | 24.6 |
| | 320 | 87.4 | 95.3 | | | |
| | 350 | 94.6 | 94.2 | | | |
| | 360 | 95.2 | 93.9 | | | |
| Example 2 (comparative example) | 300 | 80.6 | 96.6 | I (imp) | 17.80 | 17.3 |
| | 320 | 84.4 | 96.3 | | | |
| | 350 | 93.6 | 95.4 | | | |
| | 360 | 95.5 | 95.0 | | | |
| Example 3 | 300 | 89.3 | 97.6 | II (press 4) | 25.81 | 22.49 |
| | 320 | 93.7 | 97.2 | | | |
| | 340 | 97.1 | 96.7 | | | |
| | 350 | 98.2 | 96.5 | | | |
| Example 4 | 300 | 84.5 | 96.5 | II (press 4) | 17.80 | 17.3 |
| | 320 | 90.8 | 96.5 | | | |
| | 340 | 95.7 | 95.8 | | | |
| | 350 | 97.4 | 95.3 | | | |
| Example 5 | 300 | 77.9 | 96.6 | I (mill, press 4) | 17.80 | 17.3 |
| | 320 | 83.4 | 96.5 | | | |
| | 340 | 88.7 | 96.1 | | | |
| | 350 | 91.1 | 95.7 | | | |
| Example 6 | 300 | 88.2 | 97.5 | II (extr) | 25.81 | 22.49 |
| | 320 | 92.7 | 97.6 | | | |
| | 350 | 98.4 | 96.7 | | | |
| | 360 | 99.2 | 96.4 | | | |
| Example 7 | 300 | 86.6 | 98.3 | II (extr) | 25.81 | 22.49 |
| | 320 | 91.8 | 98.2 | | | |
| | 350 | 97.7 | 97.4 | | | |
| | 360 | 98.6 | 97.1 | | | |

*I: Spheralite 501A, particle size 2-5 mm; II: Spheralite 509A, particle size 7-15 μm; imp: impregnated; press 4: pressed into pellet shape at a pressure of 4 t; mill: milled (particle size after milling ≤250 μm); extr: extruded Further experimental conditions are indicated below:
GHSV: 1300 h$^{-1}$ (based on standard conditions at 0° C. and 1.013 bar in accordance with DIN 1343)
LHSV: 0.4 h$^{-1}$ (based on liquid methanol)
Mass ratio of $H_2S$/MeOH: 1.9
Pressure: 9 bar The reaction mixture obtained, which comprised the products methyl mercaptan, dimethyl sulphide, dimethyl disulphide and dimethyl ether and also the unreacted starting materials methanol and hydrogen sulphide was analysed by on-line gas chromatography.

Figure 2:
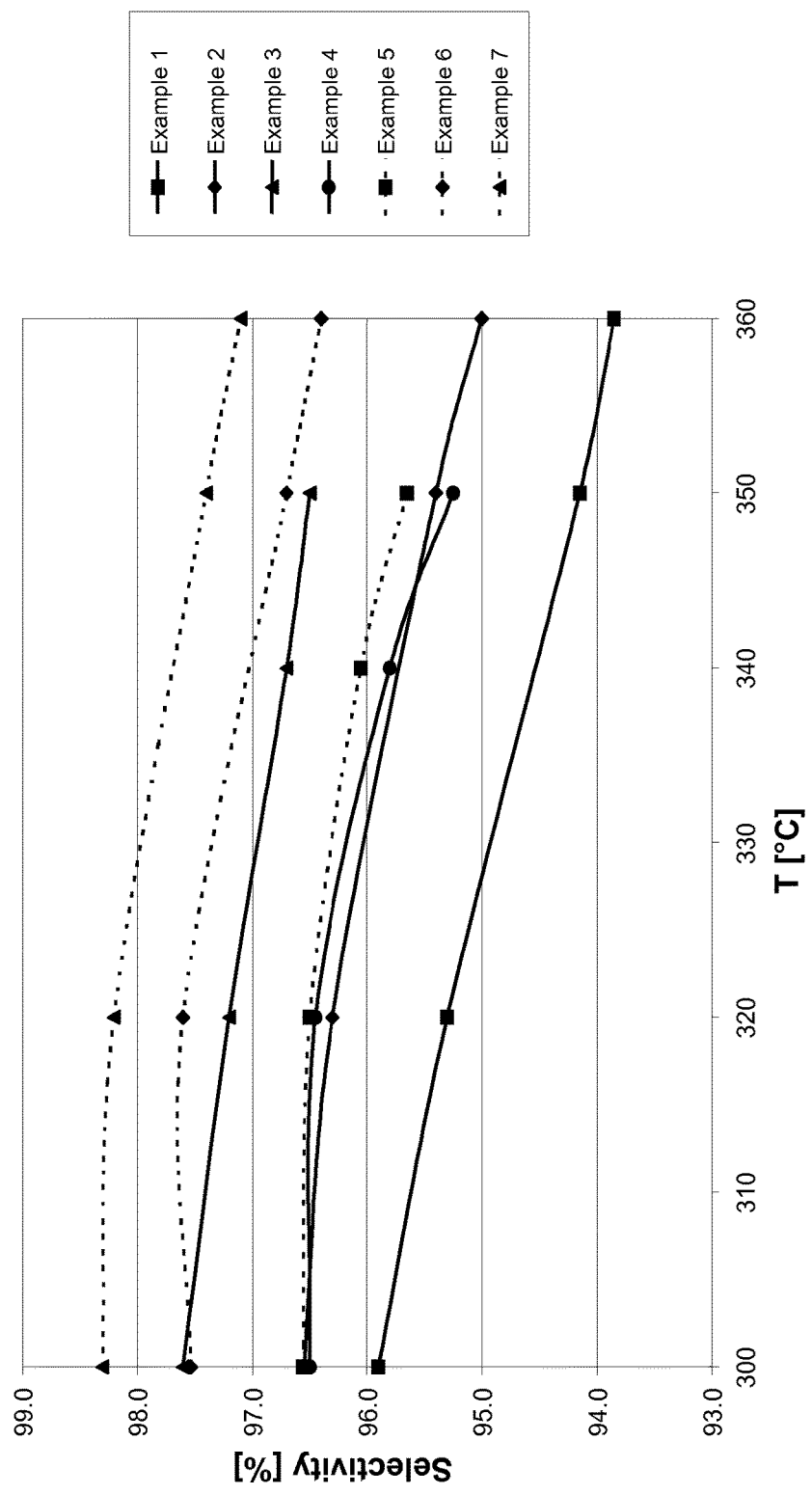
FIG. 2 shows the selectivity in the reaction of hydrogen sulphide and methanol to form methyl mercaptan achieved when using the catalysts according to the invention (Examples 3 to 7) at various temperatures under the conditions described in Example 8 compared to that achieved when using catalysts which have been produced by processes known from the prior art (Comparative Examples 1 and 2).
Figure 3:
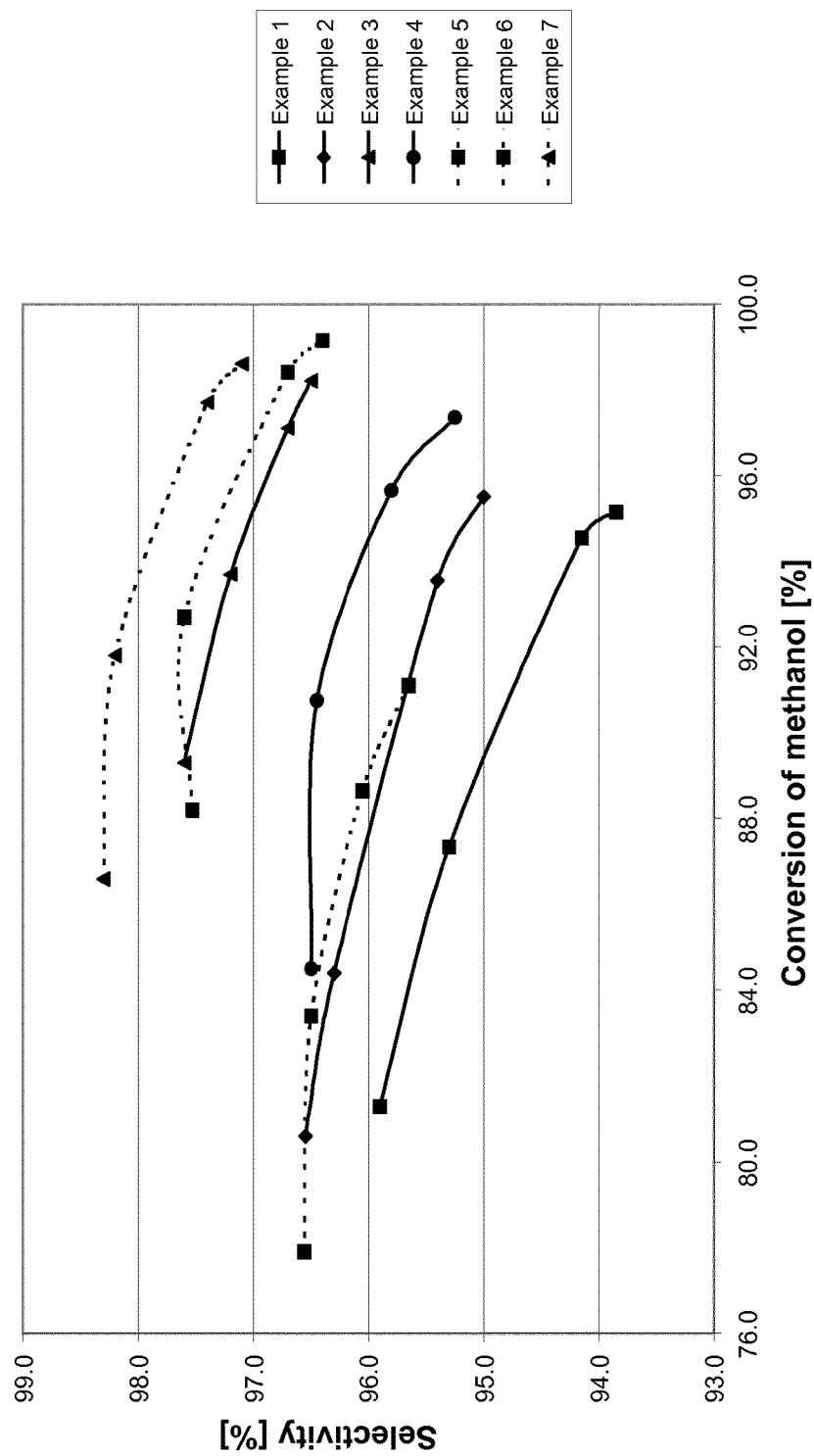
FIG. 3 shows the relationship between conversion and selectivity for the catalysts of Examples 1 to 7.

The measurement results are shown in Table 1 and also FIGS. 1 to 3.

It can be seen that a catalyst produced by the process of the invention and having a more finely divided support material displays, compared to a catalyst produced by impregnation of particles of support material having a size of 2 mm and more, a higher conversion at the same loading at a given temperature (Comparative Example 2 compared to Example 4 according to the invention) and thus a higher selectivity to methyl mercaptan at the same conversion.

Furthermore, catalysts in the form of extrudates and pressed bodies which have a high loading (for example above 45% by weight) of the oxidic composition can be produced by the production process of the invention, enabling the conversion and the selectivity of the catalysed reactions to be increased further. This is not possible at a loading above 45% by weight in the case of a catalyst produced by the impregnation process (Comparative Example 1 and Example 3 according to the invention compared to Comparative Example 2 and Example 4 according to the invention.

Addition of inorganic and/or organic binders, preferably inorganic binders, not only enables the mechanical strength of the catalyst according to the invention to be increased, but it is surprisingly also possible to observe a further increase in the selectivity and the conversion at a particular temperature (Example 6).

It can also be seen that the order of addition of the alkali metal hydroxide and the oxidic tungsten compound also influence the conversion and the selectivity of the reaction at a particular temperature (Examples 6 and 7 according to the invention).

1.2. Examples 9 and 13: Variation of the Loading

Figure 4:
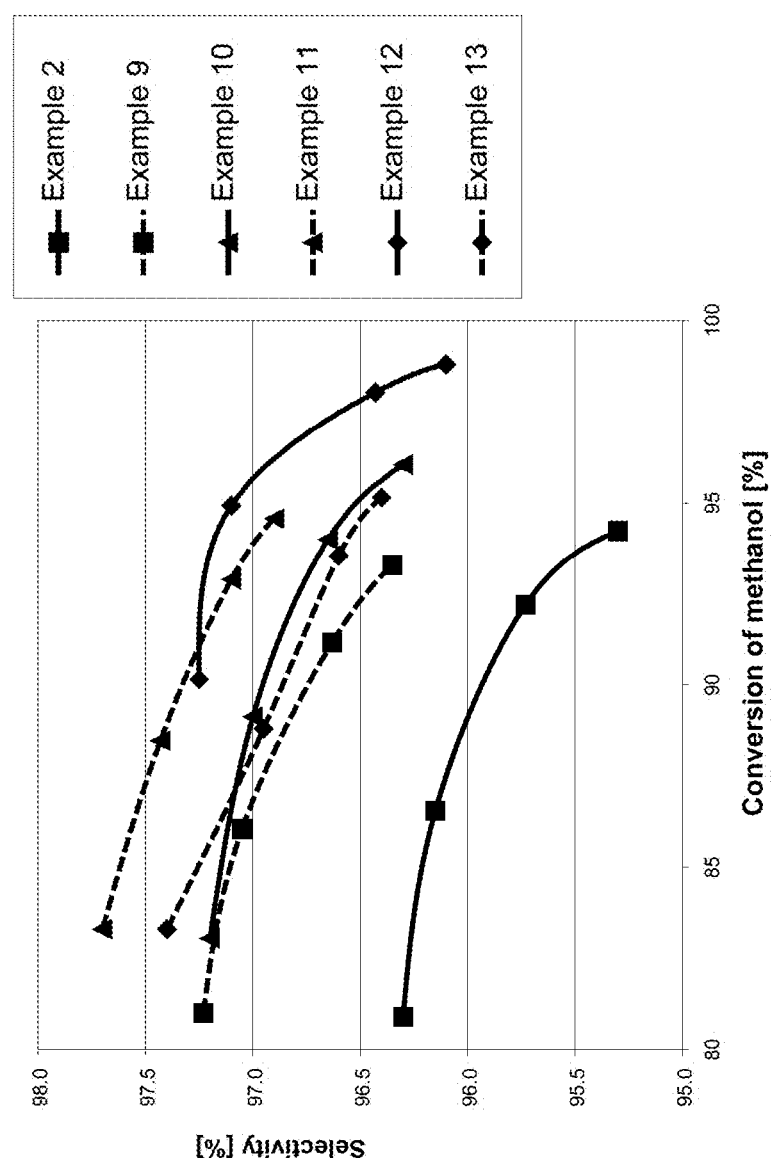
FIG. 4 shows the relationship between conversion and selectivity for catalysts according to the invention having different loadings (Examples 9 to 13) in the reaction of hydrogen sulphide and methanol to form methyl mercaptan under the conditions described in Example 8 compared to a catalyst which has been produced by a process known from the prior art (Comparative Example 2).

Example 5 was repeated with an increased loading of tungsten(VI) oxide and caesium hydroxide on the aluminium oxide. The respective loading of the catalyst and the conversion achieved therewith at a particular temperature and the selectivity achieved in a use example as per Example 8 are shown in Table 2 and also FIG. 4.

TABLE 2

| Catalyst | T [° C.] | Conversion [%] | Selectivity [%] | Support* | Loading WO$_3$ [% by wt.] | Loading Cs$_2$O [% by wt.] |
|---|---|---|---|---|---|---|
| Example 9 | 300 | 81 | 97.23 | I (mill, press 4) | 20.5 | 19.9 |
|  | 320 | 86.05 | 97.05 |  |  |  |
|  | 340 | 91.17 | 96.63 |  |  |  |
|  | 350 | 93.3 | 96.35 |  |  |  |
| Example 10 | 300 | 83.05 | 97.2 | I (mill, press 4) | 21.8 | 21.2 |
|  | 320 | 89.13 | 97 |  |  |  |
|  | 340 | 94 | 96.65 |  |  |  |
|  | 350 | 96.05 | 96.3 |  |  |  |
| Example 11 | 300 | 83.3 | 97.7 | I (mill, press 4) | 23.1 | 22.5 |
|  | 320 | 88.47 | 97.43 |  |  |  |
|  | 340 | 92.9 | 97.1 |  |  |  |
|  | 350 | 94.57 | 96.9 |  |  |  |
| Example 12 | 300 | 90.15 | 97.25 | I (mill, press 4) | 24.5 | 23.8 |
|  | 320 | 94.93 | 97.1 |  |  |  |
|  | 340 | 98.03 | 96.43 |  |  |  |
|  | 350 | 98.8 | 96.1 |  |  |  |
| Example 13 | 300 | 83.3 | 97.4 | I (mill, press 4) | 25.8 | 25.1 |
|  | 320 | 88.8 | 96.95 |  |  |  |
|  | 340 | 93.55 | 96.6 |  |  |  |
|  | 350 | 95.15 | 96.4 |  |  |  |

*I: Spheralite 501A, particle size 2-5 mm; press 4: pressed to pellet shape at a pressure of 4 bar; mill: milled (particle size after milling ≤250 μm)

It can be seen that an increase in the loading has a positive influence on the conversion and the selectivity of the catalysed reaction at a given temperature and both conversion and selectivity at a given temperature and also the selectivity of the reaction of methanol and hydrogen sulphide to form methyl mercaptan in the presence of the catalyst according to the invention can be increased by increasing the loading.

1.3. Examples 14 to 17: Influence of the Particulate Support Material

In Examples 14 to 17, various processes for producing the catalyst according to the invention were compared with one another at a loading of 23.1% by weight of WO$_3$ and 22.5% by weight of Cs$_2$O.

Example 14

Example 11 was repeated with the same loading, but the pressure in the tabletting press was 15 t instead of 4 t.

Example 15

Example 3 was repeated with a loading of 23.1% by weight of WO$_3$ and 22.5% by weight of Cs$_2$O.

Example 16

Example 11 was repeated with the same loading, but the aluminium oxide support was not milled before mixing with the tungstic acid but instead was milled together with the tungstic acid in a ball mill (from Haldenwanger Berlin) using a Schwinherr Multifix drive for 2 hours.

Example 17

Example 16 was repeated with the support material being milled with the tungstic acid for 65 hours instead of 2 hours in the ball mill.

Figure 5:
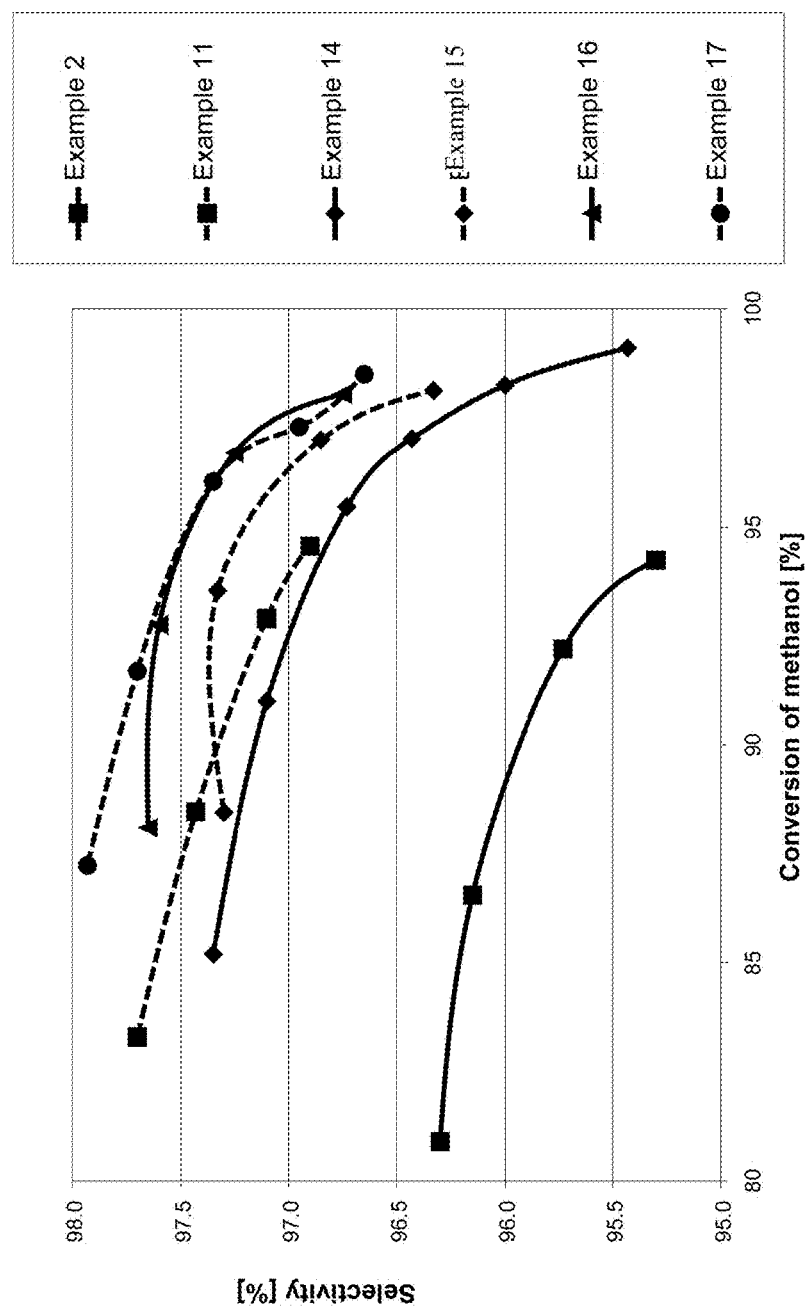
FIG. 5 shows the relationship between conversion and selectivity for various catalysts according to the invention having the same loading (Examples 11 and 14 to 17) in the case of which the catalyst composition was produced in different ways or shaping was carried out by different methods compared to a catalyst known from the prior art (Comparative Example 2) in the reaction of hydrogen sulphide and methanol to form methyl mercaptan.

The conversion and selectivity of the reaction of methanol and hydrogen sulphide to form methyl mercaptan was determined for the catalysts according to the invention of Examples 14 to 17 as described in Use Example 8. The results are shown in Table 3 and FIG. 5.

TABLE 3

| Catalyst | T [° C.] | Conversion [%] | Selectivity [%] | Support* | Loading WO$_3$ [% by wt.] | Loading Cs$_2$O [% by wt.] |
|---|---|---|---|---|---|---|
| Example 14 | 300 | 85.2 | 97.35 | I (mill, press 15) | 23.1 | 22.5 |
|  | 320 | 91 | 97.1 |  |  |  |
|  | 340 | 95.47 | 96.73 |  |  |  |
|  | 350 | 97.03 | 96.43 |  |  |  |
|  | 360 | 98.25 | 96 |  |  |  |
|  | 370 | 99.1 | 95.43 |  |  |  |
| Example 15 | 300 | 88.45 | 97.3 | II (press 4) | 23.1 | 22.5 |
|  | 320 | 93.53 | 97.33 |  |  |  |
|  | 340 | 97 | 96.85 |  |  |  |
|  | 350 | 98.13 | 96.33 |  |  |  |
| Example 16 | 300 | 88.1 | 97.65 | I (ball mill 2, press 4) | 23.1 | 22.5 |
|  | 320 | 92.75 | 97.6 |  |  |  |
|  | 340 | 96.7 | 97.25 |  |  |  |
|  | 350 | 98.05 | 96.75 |  |  |  |
| Example 17 | 300 | 87.23 | 97.93 | I (ball mill 65, press 4) | 23.1 | 22.5 |
|  | 320 | 91.7 | 97.7 |  |  |  |
|  | 340 | 96.05 | 97.35 |  |  |  |
|  | 350 | 97.3 | 96.95 |  |  |  |
|  | 360 | 98.5 | 96.65 |  |  |  |

*I: Spheralite 501A, particle size 2-5 mm; II: Spheralite 509A particle size 7-15 μm; imp: impregnated; press 4/15: pressed to pellet shape at a pressure of 4 or 15 t; ball mill 2/65: support material milled with tungstic acid for 2 or 65 h in a ball mill; mill: milled (particle size after milling ≤250 μm)

Like the preceding examples, Examples 14 to 17 also show that the present invention makes it possible to provide catalysts by means of which a selectivity of above 95% can be obtained in the reaction of methanol and hydrogen sulphide to form methyl mercaptan even at a conversion of greater than 95%. Thus, for example, a selectivity of above 95% can still be achieved at a conversion of above 99% by means of the catalyst of Example 14 at a temperature of 370° C.

A small particle size of the support material and intensive mixing of the support material, the oxidic tungsten compound and the alkali metal hydroxide, for example in a ball mill as per Example 16 or 17, have a positive effect on the conversion and the selectivity of the catalyst at a particular temperature with otherwise unchanged catalyst parameters (Examples 16 and 17 compared to Example 11).

1.4. Example 18: Energy-Dispersive X-Ray Spectroscopy

Figure 6:
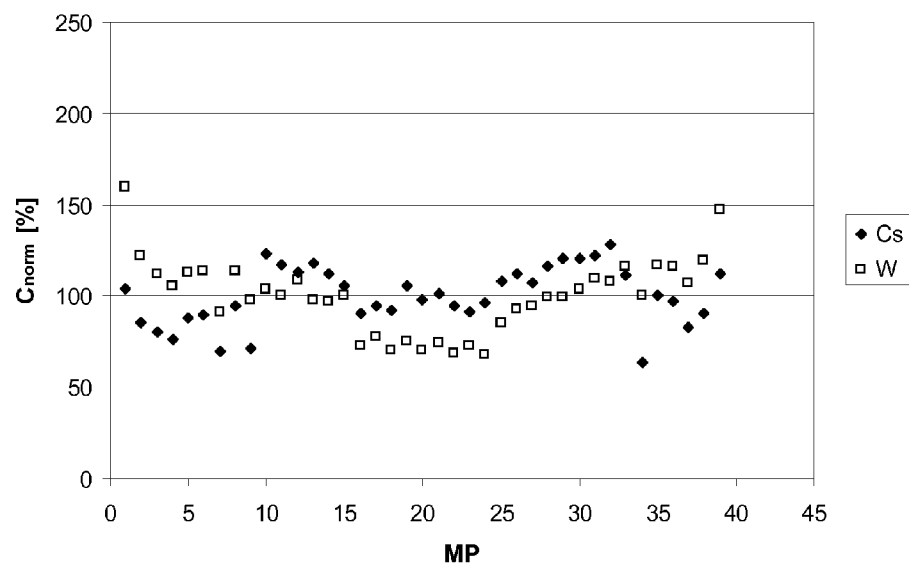
FIGS. 6 to 8 show the surface distribution of the elements caesium, tungsten and aluminium in two catalysts which have been produced by processes known from the prior art (FIG. 6: Example 1.
Figure 7:
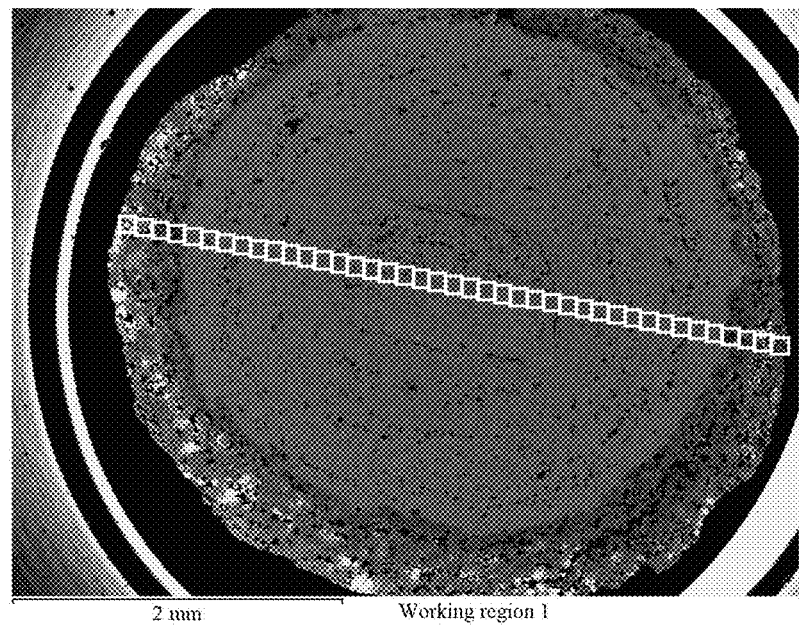
Figure 7:
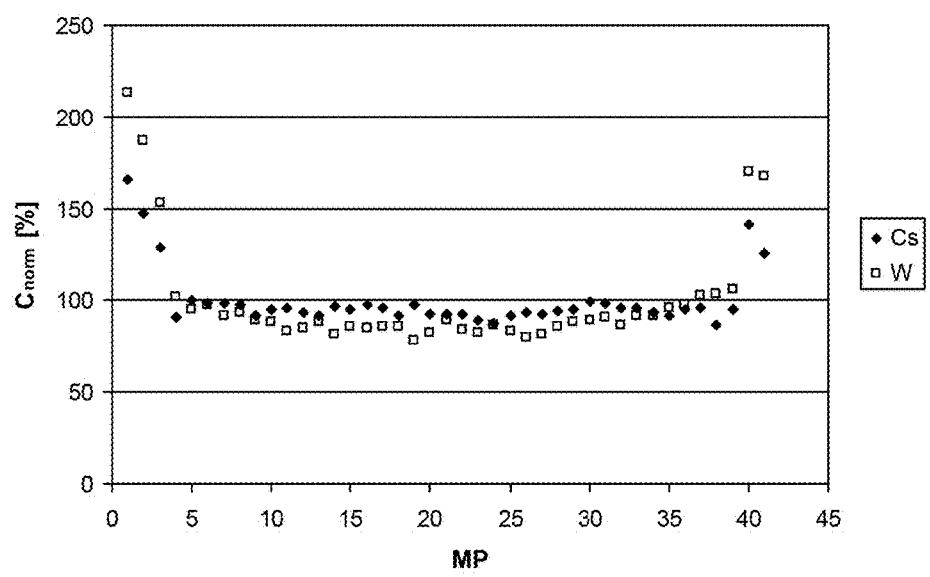
Figure 8:
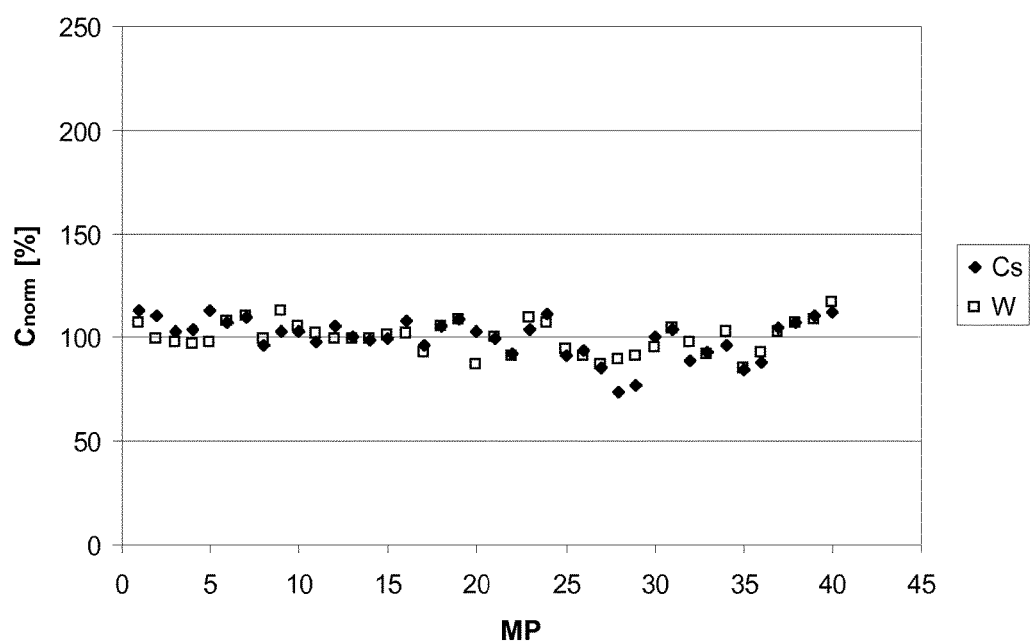

The concentration distribution of the elements aluminium, caesium and tungsten on the surface of the catalysts as per Examples 1, 2 and 6 was made visible by means of energy-dispersive X-ray spectroscopy (EDX mapping) in accordance with ISO 22309 (2006) (FIGS. 6 to 8). A Jeol 7600F scanning electron microscope (SEM) (Jeol Ltd., Tokyo, Japan) together with an Oxford INCA Energy 400 energy dispersive X-Ray analysis (EDX) system (Oxford Instruments, Abingdon, Great Britain) was used for this purpose. The scanning electron micrographs and the EDX mappings of the selected elements were recorded at a primary electron beam energy of 20 keV. The cut, embedded and polished catalyst particles were coated with a 20 nm thick carbon coating to make them electronically conductive for the analytical electron beam.

It is here surprisingly found that the elements caesium and tungsten are more homogeneously distributed in the catalyst when using the process of the invention in which the support material is preferably firstly mixed with compounds of the one element before the compound of the other element is added to this mixture than when catalyst particles are treated by the impregnation process known from the prior art with a solution containing both elements in the form of caesium tungstate.

A material contrast image of a catalyst particle is shown as respective Figure a), in which the substantial homogeneity (FIG. 8a: Example 6) or inhomogeneity (FIG. 6a) of the catalyst structure or the distribution of the elements in the particle can be seen. The respective figures b)-d) show the concentration of the elements caesium (Fig. b), tungsten (Fig. c) and aluminium (Fig. d) in the catalyst particle.

The lighter a place appears in these images, the denser the material and therefore the higher the concentration of the element concerned.

It can clearly be seen that the catalyst according to the invention (FIGS. 8a to d) displays a clearly homogenous distribution of the elements over the entire catalyst, i.e. also on the surface thereof.

To quantify this, the element distribution was determined along a straight line in the cross section of a catalyst particle by means of quantitative EDX measurements in about 40 square sections each having a side length of 100 μm. The midpoints of the squares were located on the straight line and are each 100 μm away from the midpoint of the respective adjoining square. The first and last midpoints of squares on this straight line are in each case about 100 μm away from the edge of the catalyst body. The distribution of these measurement squares over the catalyst cross section is shown in the respective figures e).

The proportion of an element was determined from the intensities of the signals in the respective square based on the sum of the proportions of all elements in this square (hereinafter referred to as concentration), with the sum in each measurement spot being 100%. From the concentrations of caesium and tungsten determined in the respective squares, the average was formed over the cross section of the specimen, i.e. over the about 40 individual values. The ratio of the experimentally determined concentration of caesium or tungsten in the respective square to the average of this concentration over the cross section of the specimen multiplied by the factor 100 will be referred to as the normalized concentration $c_{norm}$, from which the standard deviation stadev, the average deviation avdev, the largest and smallest measured value in each case (max or min) and the difference between maximum and minimum of the normalized concentrations Δ (max-min) over the cross section of the respective specimen were calculated by means of the table calculation Excel (Microsoft Office Excel 2003, Microsoft Corporation, Redmont, U.S.A.). The results are shown in Tables 4 (Example 1 which is not according to the invention), 5 (Example 2 which is not according to the invention) and 6 (Example 6 according to the invention).

TABLE 4

Quantification of the normalized concentration of caesium and tungsten over the catalyst cross section in Example 1

| MP | $c_{norm}$ (Cs) [%] | $c_{norm}$ (W) [%] | $c_{norm}$ (Cs)/ $c_{norm}$(W) |
|---|---|---|---|
| 1 | 103.31 | 159.65 | 0.65 |
| 2 | 85.44 | 122.15 | 0.70 |
| 3 | 80.13 | 112.44 | 0.71 |
| 4 | 76.01 | 105.57 | 0.72 |
| 5 | 87.64 | 113.18 | 0.77 |
| 6 | 89.13 | 113.61 | 0.78 |
| 7 | 68.99 | 90.78 | 0.76 |
| 8 | 94.38 | 113.92 | 0.83 |
| 9 | 71.26 | 98.21 | 0.73 |
| 10 | 122.95 | 103.53 | 1.19 |
| 11 | 116.79 | 100.56 | 1.16 |
| 12 | 113.24 | 108.29 | 1.05 |
| 13 | 117.99 | 98.21 | 1.20 |
| 14 | 111.89 | 96.66 | 1.16 |
| 15 | 105.44 | 100.74 | 1.05 |
| 16 | 90.41 | 72.83 | 1.24 |
| 17 | 94.87 | 77.48 | 1.22 |
| 18 | 92.11 | 70.17 | 1.31 |
| 19 | 105.58 | 75.19 | 1.40 |
| 20 | 97.92 | 69.86 | 1.40 |
| 21 | 101.47 | 74.01 | 1.37 |
| 22 | 94.52 | 68.75 | 1.37 |
| 23 | 90.97 | 72.40 | 1.26 |
| 24 | 96.08 | 67.88 | 1.42 |
| 25 | 107.85 | 84.96 | 1.27 |
| 26 | 112.11 | 92.57 | 1.21 |
| 27 | 106.79 | 94.74 | 1.13 |
| 28 | 116.15 | 99.32 | 1.17 |
| 29 | 120.05 | 99.20 | 1.21 |
| 30 | 120.54 | 103.71 | 1.16 |
| 31 | 121.82 | 109.16 | 1.12 |
| 32 | 127.70 | 107.61 | 1.19 |
| 33 | 111.54 | 116.46 | 0.96 |
| 34 | 63.68 | 99.94 | 0.64 |
| 35 | 100.19 | 116.71 | 0.86 |
| 36 | 97.29 | 116.09 | 0.84 |
| 37 | 82.75 | 106.81 | 0.77 |
| 38 | 90.62 | 119.74 | 0.76 |
| 39 | 112.39 | 146.91 | 0.77 |
| Stadev | 15.97 | 20.51 | 0.25 |
| Avdev | 13.12 | 15.22 | 0.22 |
| Max | 127.70 | 159.65 | 1.42 |
| Min | 63.68 | 67.88 | 0.64 |
| Δ (Max − Min) | 64.03 | 91.77 | 0.78 |

MP stands for square measurement spots.

TABLE 5

Quantification of the normalized concentration of caesium and tungsten over the catalyst cross section in Example 2

| MP | $c_{norm}$ (Cs) [%] | $c_{norm}$ (W) [%] | $c_{norm}$ (Cs)/$c_{norm}$(W) |
|---|---|---|---|
| 1 | 166.40 | 213.91 | 0.78 |
| 2 | 147.14 | 187.15 | 0.79 |
| 3 | 128.88 | 153.28 | 0.84 |
| 4 | 91.08 | 101.77 | 0.90 |
| 5 | 99.89 | 94.92 | 1.05 |
| 6 | 98.05 | 97.83 | 1.00 |
| 7 | 98.05 | 91.19 | 1.08 |
| 8 | 97.76 | 93.27 | 1.05 |
| 9 | 91.65 | 89.32 | 1.03 |
| 10 | 94.85 | 88.36 | 1.07 |
| 11 | 95.70 | 82.69 | 1.16 |
| 12 | 93.29 | 84.35 | 1.11 |
| 13 | 91.87 | 88.49 | 1.04 |
| 14 | 96.41 | 81.24 | 1.19 |
| 15 | 95.13 | 85.25 | 1.12 |
| 16 | 97.83 | 85.11 | 1.15 |
| 17 | 95.56 | 85.25 | 1.12 |
| 18 | 91.51 | 85.59 | 1.07 |
| 19 | 97.48 | 78.33 | 1.24 |
| 20 | 92.58 | 82.20 | 1.13 |
| 21 | 92.01 | 88.91 | 1.03 |
| 22 | 92.43 | 83.52 | 1.11 |
| 23 | 89.38 | 82.48 | 1.08 |
| 24 | 87.11 | 86.77 | 1.00 |
| 25 | 91.44 | 82.69 | 1.11 |
| 26 | 93.50 | 79.51 | 1.18 |
| 27 | 92.36 | 80.96 | 1.14 |
| 28 | 93.93 | 85.73 | 1.10 |
| 29 | 94.49 | 88.01 | 1.07 |
| 30 | 98.90 | 88.56 | 1.12 |
| 31 | 98.26 | 90.43 | 1.09 |
| 32 | 95.35 | 86.35 | 1.10 |
| 33 | 95.63 | 91.88 | 1.04 |
| 34 | 93.00 | 91.88 | 1.01 |
| 35 | 91.79 | 95.34 | 0.96 |
| 36 | 95.28 | 97.07 | 0.98 |
| 37 | 95.63 | 102.74 | 0.93 |
| 38 | 86.32 | 103.77 | 0.83 |
| 39 | 95.13 | 106.12 | 0.90 |
| 40 | 141.32 | 170.14 | 0.83 |
| 41 | 125.61 | 167.66 | 0.75 |
| Stadev | 16.88 | 31.20 | 0.12 |
| Avdev | 10.21 | 19.83 | 0.09 |
| Max | 166.40 | 213.91 | 1.24 |
| Min | 86.32 | 78.33 | 0.75 |
| Δ (Max − Min) | 80.07 | 135.58 | 0.50 |

TABLE 6

Quantification of the normalized concentration of caesium and tungsten over the catalyst cross section in Example 6

| MP | $c_{norm}$ (Cs) [%] | $c_{norm}$ (W) [%] | $c_{norm}$ (Cs)/$c_{norm}$ (W) |
|---|---|---|---|
| 1 | 112.60 | 107.38 | 1.05 |
| 2 | 110.31 | 99.52 | 1.11 |
| 3 | 102.72 | 97.71 | 1.05 |
| 4 | 103.75 | 97.24 | 1.07 |
| 5 | 112.52 | 97.71 | 1.15 |
| 6 | 106.75 | 108.11 | 0.99 |
| 7 | 109.67 | 110.64 | 0.99 |
| 8 | 95.85 | 99.31 | 0.97 |
| 9 | 102.48 | 112.97 | 0.91 |
| 10 | 103.19 | 105.73 | 0.98 |
| 11 | 97.82 | 101.85 | 0.96 |
| 12 | 105.72 | 99.26 | 1.07 |
| 13 | 100.43 | 99.57 | 1.01 |
| 14 | 99.01 | 99.78 | 0.99 |
| 15 | 99.80 | 101.49 | 0.98 |
| 16 | 107.70 | 101.74 | 1.06 |
| 17 | 96.56 | 92.59 | 1.04 |
| 18 | 105.56 | 105.16 | 1.00 |
| 19 | 108.73 | 108.42 | 1.00 |
| 20 | 102.56 | 87.05 | 1.18 |
| 21 | 99.56 | 100.14 | 0.99 |
| 22 | 92.37 | 91.35 | 1.01 |
| 23 | 104.06 | 109.45 | 0.95 |
| 24 | 111.10 | 106.61 | 1.04 |
| 25 | 91.18 | 94.55 | 0.96 |
| 26 | 93.24 | 90.73 | 1.03 |
| 27 | 85.34 | 86.85 | 0.98 |
| 28 | 73.88 | 89.28 | 0.83 |
| 29 | 77.04 | 91.35 | 0.84 |
| 30 | 100.35 | 95.23 | 1.05 |
| 31 | 103.98 | 104.80 | 0.99 |
| 32 | 88.50 | 97.81 | 0.90 |
| 33 | 92.61 | 92.33 | 1.00 |
| 34 | 96.32 | 102.68 | 0.94 |
| 35 | 84.86 | 85.40 | 0.99 |
| 36 | 87.79 | 92.85 | 0.95 |
| 37 | 104.77 | 102.78 | 1.02 |
| 38 | 106.91 | 107.38 | 1.00 |
| 39 | 109.99 | 108.57 | 1.01 |
| 40 | 112.44 | 116.64 | 0.96 |
| Stadev | 9.48 | 7.62 | 0.07 |
| Avdev | 7.41 | 6.13 | 0.05 |
| Max | 112.60 | 116.64 | 1.18 |
| Min | 73.88 | 85.40 | 0.83 |
| Δ (Max − Min) | 38.72 | 31.24 | 0.35 |

It can clearly be seen that standard deviation and average deviation of both the caesium distribution and the tungsten distribution over the catalyst are significantly smaller in the catalyst according to the invention of Example 6. The difference between the maximum and minimum of the concentration determined in each case is also significantly smaller in the catalyst according to the invention. In addition, the ratio of the normalized caesium concentration to the normalized tungsten concentration $c_{norm}$ (Cs)/$c_{norm}$ (W) in the catalyst according to the invention is also significantly more uniform over the catalyst cross section, as indicated by the standard deviation and the average deviation of this value and also the difference between maximum and minimum value for the respective catalysts.

These quantitative measurements confirm the significantly more homogeneous distribution of the elements caesium and tungsten over the entire catalyst.

The invention claimed is:

1. A process for producing a catalyst comprising a support material, wherein the support material has a particle size from 1-25 μm, and an oxidic composition comprising oxygen together with at least one alkali metal and tungsten, wherein the oxidic composition has a formula $A_xWO_y$, wherein A is at least one alkali metal, x is from 0.8 to 2 and represents the mole fraction of the alkali metal to tungsten in the composition, and y is from 3.4 to 4 and represents the mole fraction of oxygen in the composition, the process comprising:
   1) mixing of the support material with an oxidic tungsten compound and at least one separate alkali metal compound to obtain a catalyst composition; and
   2) shaping of the catalyst composition.

2. The process of claim 1, wherein the oxidic tungsten compound is selected from the group consisting of tungsten trioxide ($WO_3$), tungstic acid ($WO_3.H_2O$), metatungstic acid, paratungstic acid, isopolytungstic acids, heteropolytungstic acids, ammonium salts thereof, hydrates thereof and mixtures thereof, ammonium orthotungstate, ammonium metatungstate and ammonium paratungstate.

3. The process of claim 1, wherein at least one alkali metal compound is a basic alkali metal compound.

4. The process of claim 1, wherein the support material is an oxidic inorganic support material.

5. The process of claim 1, wherein the oxidic tungsten compound and the separate alkali metal compound are added in succession to the support material.

6. The process of claim 1, wherein at least one organic and/or inorganic binder is added in one or both of 1) and 2).

7. The process of claim 1, wherein the shaping of the catalyst is carried out by extrusion or pressing.

8. The process of claim 3, wherein the basic alkali metal compound is selected from the group consisting of a hydroxide of an alkali metal and a carbonate of an alkali metal.

9. The process of claim 4, wherein the support material is selected from the group consisting of aluminium oxide, silicon dioxide, titanium dioxide, zirconium oxide, and amorphous aluminosilicates and mixtures thereof.

10. The process of claim 5, wherein the oxidic tungsten compound is added as a solid to the support material or to the mixture of support material and a least one alkali metal compound.

11. The process of claim 7, further comprising:
(i) drying of the catalyst composition and/or of the shaped catalyst; and
(ii) calcination of the catalyst composition and/or of the shaped catalyst.

12. A catalyst, comprising:
a support material having a particle size from 1-25 μm; and
an oxidic composition comprising oxygen together with at least one alkali metal and tungsten, wherein the oxidic composition has a formula $A_xWO_y$, wherein A is at least one alkali metal, x is from 0.8 to 2 and represents the mole fraction of the alkali metal to tungsten in the composition, and y is from 3.4 to 4 and represents the mole fraction of oxygen in the composition.

13. The catalyst of claim 12, wherein the catalyst is produced by a process comprising:
mixing a solid tungsten compound with the support material.

14. The catalyst of claim 12, wherein the proportion of the oxidic composition composed of alkali metal and tungsten in the catalyst is greater than 15% by weight, based on the total weight of the catalyst.

15. The catalyst of claim 12, wherein the support material comprises at least one oxidic inorganic compound.

16. The catalyst of claim 12, which further comprises at least one organic and/or inorganic binder.

17. The catalyst of claim 12, wherein a standard deviation, stadev, of the normalized tungsten concentration, $c_{norm}$ (W), over the cross section of the catalyst is less than 20, determined by quantitative EDX analysis in accordance with ISO 22309 (2006) in square measurement spots, which have a side length of 100 μm in each case and whose midpoints lie on a straight line and are in each case 100 μm from the midpoint of the adjoining square, with the first and last midpoint of a square being in each case 100 μm from the edge of the catalyst cross section.

18. A catalyst comprising, based on a total weight of the catalyst:
from 25% to 50% by weight of a support material having a particle size from 1-25 μm; and
greater than 40% by weight of an oxidic composition comprising oxygen together with at least one alkali metal and tungsten.

* * * * *